(12) United States Patent
Steemers et al.

(10) Patent No.: US 12,104,281 B2
(45) Date of Patent: Oct. 1, 2024

(54) ANALYSIS OF MULTIPLE ANALYTES USING A SINGLE ASSAY

(71) Applicant: ILLUMINA, INC., San Diego, CA (US)

(72) Inventors: Frank J. Steemers, Encinitas, CA (US); Fan Zhang, San Diego, CA (US); Dmitry K. Pokholok, San Diego, CA (US); Steven Norberg, La Mesa, CA (US)

(73) Assignee: ILLUMINA, INC., San Diego, CA (US)

( * ) Notice: Subject to any disclaimer, the term of this patent is extended or adjusted under 35 U.S.C. 154(b) by 580 days.

(21) Appl. No.: 17/250,848

(22) PCT Filed: Nov. 25, 2019

(86) PCT No.: PCT/US2019/062945
§ 371 (c)(1),
(2) Date: Mar. 11, 2021

(87) PCT Pub. No.: WO2020/112604
PCT Pub. Date: Jun. 4, 2020

(65) Prior Publication Data
US 2022/0195504 A1    Jun. 23, 2022

Related U.S. Application Data

(60) Provisional application No. 62/773,862, filed on Nov. 30, 2018.

(51) Int. Cl.
*C40B 50/06* (2006.01)
*C12Q 1/6806* (2018.01)
*C12Q 1/6834* (2018.01)

(52) U.S. Cl.
CPC ............ *C40B 50/06* (2013.01); *C12Q 1/6806* (2013.01); *C12Q 1/6834* (2013.01); *C12Q 2563/179* (2013.01)

(58) Field of Classification Search
None
See application file for complete search history.

(56) References Cited

U.S. PATENT DOCUMENTS

| | | | |
|---|---|---|---|
| 5,130,238 | A | 7/1992 | Malek et al. |
| 5,185,243 | A | 2/1993 | Ullman et al. |

(Continued)

FOREIGN PATENT DOCUMENTS

| | | |
|---|---|---|
| CN | 106319639 | 1/2017 |
| CN | 106459967 | 2/2017 |

(Continued)

OTHER PUBLICATIONS

Extended European search report dated Dec. 15, 2023 in application No. 23192005.9.

(Continued)

*Primary Examiner* — Christian C Boesen
(74) *Attorney, Agent, or Firm* — KNOBBE, MARTENS, OLSON & BEAR, LLP

(57) ABSTRACT

Embodiments of systems, methods, and compositions provided herein relate to methods of simultaneously analyzing multiple analytes in a single sample using a single assay. Some embodiments relate to simultaneous analysis of DNA and RNA in a single sample, for example, to the simultaneous generation of DNA and RNA libraries.

14 Claims, 18 Drawing Sheets

Specification includes a Sequence Listing.

(56) References Cited

U.S. PATENT DOCUMENTS

| | | |
|---|---|---|
| 5,455,166 A | 10/1995 | Walker |
| 5,573,907 A | 11/1996 | Carrino et al. |
| 5,679,524 A | 10/1997 | Nikiforov et al. |
| 5,925,545 A | 7/1999 | Reznikoff et al. |
| 5,965,443 A | 10/1999 | Reznikoff |
| 6,210,891 B1 | 4/2001 | Nyren et al. |
| 6,214,587 B1 | 4/2001 | Dattagupta et al. |
| 6,258,568 B1 | 7/2001 | Nyren |
| 6,274,320 B1 | 8/2001 | Rothberg et al. |
| 6,355,431 B1 | 3/2002 | Chee et al. |
| 6,890,741 B2 | 5/2005 | Fan et al. |
| 6,913,884 B2 | 7/2005 | Stuelpnagel et al. |
| 7,001,792 B2 | 2/2006 | Sauer et al. |
| 7,057,026 B2 | 6/2006 | Barnes et al. |
| 7,083,980 B2 | 8/2006 | Reznikoff et al. |
| 7,115,400 B1 | 10/2006 | Adessi et al. |
| 7,211,414 B2 | 5/2007 | Hardin et al. |
| 7,244,559 B2 | 7/2007 | Rothberg et al. |
| 7,315,019 B2 | 1/2008 | Turner et al. |
| 7,329,492 B2 | 2/2008 | Hardin et al. |
| 7,405,281 B2 | 7/2008 | Xu et al. |
| 7,582,420 B2 | 9/2009 | Oliphant et al. |
| 7,595,883 B1 | 9/2009 | El Gamal et al. |
| 7,608,434 B2 | 10/2009 | Reznikoff et al. |
| 7,611,869 B2 | 11/2009 | Fan |
| 7,670,810 B2 | 3/2010 | Gunderson et al. |
| 7,985,565 B2 | 7/2011 | Mayer et al. |
| 8,003,354 B2 | 8/2011 | Shen et al. |
| 9,040,256 B2 | 5/2015 | Grunenwald et al. |
| 9,080,211 B2 | 7/2015 | Grunenwald et al. |
| 9,115,396 B2 | 8/2015 | Grunenwald et al. |
| 2005/0053980 A1 | 3/2005 | Gunderson et al. |
| 2005/0181440 A1 | 8/2005 | Chee et al. |
| 2005/0191698 A1 | 9/2005 | Chee et al. |
| 2008/0108082 A1 | 5/2008 | Rank et al. |
| 2009/0026082 A1 | 1/2009 | Rothberg et al. |
| 2009/0127589 A1 | 5/2009 | Rothberg et al. |
| 2009/0186349 A1 | 7/2009 | Gunderson et al. |
| 2010/0137143 A1 | 6/2010 | Rothberg et al. |
| 2010/0282617 A1 | 11/2010 | Rothberg et al. |
| 2011/0059865 A1 | 3/2011 | Smith et al. |
| 2012/0301925 A1 | 11/2012 | Belyaev |
| 2013/0143774 A1 | 6/2013 | Actis et al. |
| 2014/0194324 A1 | 7/2014 | Gormley et al. |

FOREIGN PATENT DOCUMENTS

| | | |
|---|---|---|
| CN | 106536735 | 3/2017 |
| CN | 106661561 | 5/2017 |
| CN | 107250379 | 10/2017 |
| CN | 107969137 | 4/2018 |
| CN | 108350497 | 7/2018 |
| EP | 0 320 308 B1 | 6/1989 |
| EP | 0 336 731 B1 | 10/1989 |
| EP | 0 439 182 B1 | 4/1996 |
| RU | 2015120176 | 1/2017 |
| RU | 2609630 C2 | 2/2017 |
| WO | WO 89/09835 | 10/1989 |
| WO | WO 89/12696 | 12/1989 |
| WO | WO 90/01069 | 2/1990 |
| WO | WO 91/06678 | 5/1991 |
| WO | WO 95/23875 | 9/1995 |
| WO | WO 01/009363 | 2/2001 |
| WO | WO 04/018497 | 3/2004 |
| WO | WO 07/123744 | 11/2007 |
| WO | WO 10/048605 | 4/2010 |
| WO | WO 12/058096 | 5/2012 |
| WO | WO 14/189957 | 11/2014 |
| WO | WO 15/160895 | 10/2015 |
| WO | WO 2016/130704 A2 | 8/2016 |
| WO | WO 2018/064640 A1 | 4/2018 |
| WO | WO 18/208804 | 11/2018 |
| WO | WO 2018/218226 A1 | 11/2018 |
| WO | WO 19/152108 | 8/2019 |
| WO | WO 19/157529 | 8/2019 |
| WO | WO 19/212615 | 11/2019 |
| WO | WO 2019/213294 | 11/2019 |

OTHER PUBLICATIONS

Notice of reasons for rejection dated Nov. 22, 2023 in Japanese patent application No. 2021-515465, 10 pp.

Official action dated Aug. 30, 2023 in Russian patent application No. 2021108043/10(017338), 24 pp.

Official action dated Jan. 15, 2024 in Russian patent application No. 2021108043/10(017338), 10 pp.

Amini et al., Dec. 2014, Haplotype-resolved whole genome sequencing by contiguity preserving transposition and combinatorial indexing, Nat Genet, 46:1343-1349.

Appleby et al., 2009, New technologies for ultra-high throughput genotyping in plants, Methods Mol Biol., 513:19-39.

Bentley, D.R. et al., "Accurate whole human genome sequencing using reversible terminator chemistry," Nature 2008, 456, 53-59.

Boeke et al., 1989, Transcription and reverse transcription of retrotransposons, Ann. Rev. Microbiol. 43:403-434.

Brown et al., Apr. 1989, Retroviral integration: structure of the initial covalent product and its precursor, and a role for the viral IN protein, Proc. Natl. Acad. Sci. USA, 86:2525-2529.

Buenrostro et al. Dec. 2013, Transposition of native chromatin for multimodal regulatory analysis and personal epigenomics, Nature Methods, 10(12):1213-1218.

Cockroft et al., Jan. 23, 2008, A single-molecule nanopore device detects DNA polymerase activity with single-nucleotide resolution, J. Am. Chem. Soc., 130(3):818-820.

Colegio et al., Apr. 2001, In vitro transposition system for efficient generation of random mutants of campylobacter jejuni, J. Bacteriol., 183:2384-2388.

Craig, 1996, Transposon Tn7, Curr. Top. Microbiol. Immunol., 204:27-48.

Craig, Mar. 15, 1996, V(D)J recombination and transposition: closer than expected, Science, 271:1512.

Deamer et al., 2002, Characterization of nucleic acids by nanopore analysis, Acc. Chem. Res. 35:817-825.

Deamer et al., Apr. 2000, Nanopores and nucleic acids: prospects for ultrarapid sequencing, Trends Biotechnol. 18:147-151.

Dean et al., Apr. 16, 2002, Comprehensive human genome amplification using multiple displacement amplification, Proc. Natl. Acad. Sci. USA 99(8):5261-5266.

Devine et al., 1994, Efficient integration of artificial transposons into plasmid targets in vitro: a useful tool for DNA mapping, sequencing and genetic analysis, Nucleic Acids Res., 22(18):3765-3772.

Fox et al. 2009, Applications of ultra-high-throughput sequencing, Methods Mol Biol., 553:79-108.

Gloor, 2004, Gene targeting in *Drosophila*, Methods Mol. Biol., 260:97-114.

Goryshin et al., Mar. 27, 1998, Tn5 in vitro transposition, J. Biol. Chem. 273:7367-7374.

Grothues et al., 1993, PCR amplification of megabase DNA with tagged random primers (T-PCR), Nucleic Acids Res. 21(5):1321-1322.

Healy, 2007, Nanopore-based single-molecule DNA analysis, Nanomed. 2(4):459-481.

Ichikawa et al., Nov. 5, 1990, In vitro transposition of Transposon Tn3*, J. Biol. Chem., 265:18829-18832.

Imelfort et al., 2009, De novo sequencing of plant genomes using second-generaiton technologies, Brief Bioinform, 10(6):609-618.

Kirby et al., 2002, Cryptic plasmids of *Mycobacterium avium*: Tn552 to the rescue, Mol. Microbiol., 43(1):173-186.

Kleckner et al., 1996, Tn10 and IS10 transposition and chromosome rearrangements: mechanism and regulation in vivo and in vitro, Curr. Top. Microbiol. Immunol., 204:49-82.

Korlach et al. Jan. 29, 2008, Selective aluminum passivation for targeted immobilization of single DNA polymerase molecules in zero-mode waveguide nanostructures, Proc. Natl. Acad. Sci. USA, 105(4):1176-1181.

(56) References Cited

OTHER PUBLICATIONS

Lage et al., 2003, Whole genome analysis of genetic alterations in small DNA samples using hyperbranched strand displacement amplification and array-CGH, Genome Research, 13:294-307.
Lampe et al., 1996, A purified mariner transposase is sufficient to mediate transposition in vitro, EMBO J., 15:5470-5479.
Levene et al., Jan. 31, 2003, Zero-mode waveguides for single-molecule analysis at high concentrations, Science 299:682-686.
Li et al. 2003, DNA molecules and configurations in a solid-state nanopore microscope, Nat. Mater. 2:611-615.
Lundquist et al. May 1, 2008, Parallel confocal detection of single molecules in real time, Opt. Lett. 33(9):1026-1028.
Margulies et al., Sep. 15, 2025, Genome sequencing in open microfabricated high density picoliter reactors, Nature, 437:376-80.
Mizuuchi, Dec. 1983, In vitro transposition of bacteriophage mu: a biochemical approach to a novel replication reaction, Cell, 35:785-794.
Morozova et al., 2008, Applications of next-generation sequencing technologies in functional genomics, Genomics, 92:255-64.
Ohtsubo 1996, Bacterial insertion sequences, Curr. Top. Microbiol. Immunol. 204:1-26.
Plasterk, 1996, The Tc1/mariner transposon family, Curr. Top. Microbiol. Immunol., 204:125-143.
Reznikoff et al., Biochem. Biophys. Res. Commun. 1999, 266, 729-734).
Ronaghi et al. Jul. 17, 1998, A sequencing method based on real-time pyrophosphate, Science, 281(5375):363-365.
Ronaghi et al., 1996, Real-time DNA sequencing using detection of pyrophosphate release, Analytical Biochemistry, 242:84-89.
Ronaghi, 2001, Pyrosequencing sheds light on DNA sequencing, Genome Res. 11(1):3-11.
Savilahti et al., 1995, The phage mu transpososome core: DNA requirements for assembly and function, EMBO J., 14:4893-4903.
Shendure et al., Sep. 9, 2005, Accurate multiplex polony sequencing of an evolved bacterial genome, Science, 309:1728-1732.
Soni et al. 2007, Progress toward ultrafast DNA sequencing using solid-state nanopores, Clin. Chem. 53(11):1996-2001.
Walker et al., 1992, Strand displacement amplification-an isotherma, in vitro DNA amplification technique, Nucl. Acids Res. 20(7):1691-1696.
Walker et al., 1995, A chemiluminescent DNA probe test based on strand displacement amplification, in Wsiedbrauk et al., eds., Molecular Methods for Virus Detection, Academic Press, Inc., pp. 330 349.
Wilson et al., 2007, New transposon delivery plasmids for insertiaonl mutagenesis in bacillus anthracis, J. Microbiol. Methods, 71:332-335.
Zhang et al., Oct. 2009, A novel mechanism of transposon-mediate gene activation, PLoS Genet. 5(10):e1000689.
Reuter et al., "Simul-seq: combined DNA and RNA sequencing for whole-genome and transcriptome profiling", Nature Methods, vol. 13. No. 11, Nov. 1, 2016 (Nov. 1, 2016), pp. 953-958.
International Search Report issued in application No. PCT/US2019/062945, dated Feb. 27, 2020.

1. Transposition into Chromatin (contiguity–preserving transposition or CPT)

2. Droplet Partitioning

1. Cleave Primers (UDG)
2. PCR

3. Indexed Primer Pool (Nextera)

- B15-P7 (solution)
- P5
- Barcode
- A14 Nextera Adapter
- Hydrogel bead

Cell Lysis &
Nuclei Isolation

DNA
Tagmentation

Biotin Capture
Probe Hybridzation

A

B 0.5X = 2.5ul TDE1 = 6.55 nM final
1X = 5ul TDE1 = 13.1 nM final (standard)
2X = 10ul TDE1 = 26.2 nM final

ANALYSIS OF MULTIPLE ANALYTES USING A SINGLE ASSAY

FIELD

Systems, methods, and compositions provided herein relate to assays for simultaneously analyzing multiple analytes in a single sample. Specifically, the aspects disclosed herein relate to methods of analyzing DNA and RNA from a single sample in a single assay.

BACKGROUND

The detection of specific nucleic acid sequences present in a biological sample has been used, for example, as a method for identifying and classifying microorganisms, diagnosing infectious diseases, detecting and characterizing genetic abnormalities, identifying genetic changes associated with cancer, studying genetic susceptibility to disease, and measuring response to various types of treatment. A common technique for detecting specific nucleic acid sequences in a biological sample is nucleic acid sequencing.

Whole genome sequencing, genotyping, targeted resequencing, gene expression, single cell genomics, epigenomics, and protein expression analyses of tissue samples can be of significant importance for identifying disease biomarkers, accurately diagnosing and prognosticating diseases, and selecting the proper treatment for a patient. Often, this requires multiple assays for separately analyzing a specific analyte of interest, such as DNA, RNA, or proteins. Different assays of been established to separately and individually analyze these analytes. However, a comprehensive analysis of multiple analytes is time consuming and tedious.

SUMMARY

The present disclosure is related to systems, methods, and compositions for simultaneously analyzing multiple analytes in a sample using a single assay.

Some embodiments provided herein relate to nucleic acid libraries. In some embodiments, the libraries comprise a complementary DNA (cDNA) library and a genomic DNA (gDNA) library. In some embodiments, the cDNA library is derived from mRNA molecules and comprises nucleic acids having a first tag comprising a first barcode. In some embodiments, the gDNA library is derived from genomic DNA and comprises nucleic acids having a second tag comprising a second barcode. In some embodiments, the first barcode and the second barcode are the same or different and the first barcode and second barcode identify a common source of the cDNA and gDNA libraries. In some embodiments, the cDNA and gDNA libraries are co-compartmentalized and prepared in the same environment. In some embodiments, the tag for DNA and the tag for RNA is the same.

Some embodiments provided herein relate to a flowcell device. In some embodiments, the flowcell device comprises a first probe for capturing RNA, wherein the first probe comprises a first barcode and a first substrate recognition sequence and a second probe for capturing DNA, wherein the second probe comprises a second barcode and a second substrate recognition sequence. In some embodiments, the first barcode and the second barcode are the same or different, and the first barcode and the second barcode identify a common source of the RNA and DNA. In some embodiments, the first and second probes are configured to simultaneously analyze in a single compartment RNA and DNA from a sample. The method of claim 19, wherein the first and second capture probes are immobilized on a solid support.

Some embodiments provided herein relate to methods of simultaneously analyzing in a single compartment DNA and RNA a sample. In some embodiments, the methods include providing a sample comprising DNA and RNA, wherein the RNA comprises a first tag, differentially tagging DNA with a second tag, contacting the sample in a single compartment with a first capture probe for capturing the RNA and a second capture probe for capturing the tagged DNA, hybridizing the first capture probe to the RNA and the second capture probe to the DNA, thereby capturing RNA and DNA, and analyzing DNA and RNA. In some embodiments, the first capture probe comprises a first barcode and the second capture probe comprises a second barcode, and the first barcode and the second barcode identify a common source of the RNA and DNA.

Some embodiments provided herein relate to methods of simultaneously generating in a single compartment a nucleic acid library comprising gDNA and cDNA. In some embodiments, the methods include providing a sample comprising DNA and RNA, wherein the RNA comprises a first tag, differentially tagging DNA with a second tag, contacting in a single compartment the sample with a first probe for capturing the RNA and a second probe for capturing the tagged DNA, hybridizing the RNA and the DNA to the first and second probes, respectively, and simultaneously generating a cDNA library and gDNA library from the hybridized RNA and DNA. In some embodiments, the first probe comprises a first barcode and the second probe comprises a second barcode, and the first barcode and the second barcode identify a common source of the RNA and DNA.

Some embodiments provided herein relate to kits for simultaneously analyzing in a single compartment DNA and RNA in a sample. In some embodiments, the kits include transposition reagents and a first probe complementary to a first tag and a second probe complementary to a second tag, wherein the first and second probes are immobilized on a solid support, wherein the first probe comprises a first barcode and the second probe comprises a second barcode, and wherein the first and second barcode identify a common source of the DNA and RNA.

Some embodiments provided herein relate to methods of performing single cell ATAC-seq analysis. In some embodiments, the methods include providing a sample comprising a population of cells or nuclei, performing contiguity preserving transposition on target nucleic acids, partitioning the population of cells or nuclei into individual droplets, wherein a single cell or nucleus is partitioned into a single droplet, indexing the target nucleic acids, and analyzing the indexed nucleic acids.

Some embodiments provided herein relate to methods of combinatorial indexing (CPT-seq). In some embodiments, the methods include providing a sample comprising a population of cells or nuclei, performing individually indexed contiguity preserving transposition on target nucleic acids, partitioning the population of cells or nuclei into individual droplets, wherein multiple cells or nuclei are partitioned into a single droplet, and wherein the multiple cells or nuclei within a single droplet have a unique index, indexing the target nucleic acids, and analyzing the indexed nucleic acids.

In any of the embodiments summarized herein, the analytes are obtained from a population of cells, a single cell, a population of cell nuclei, or a cell nucleus. In any of the embodiments summarized herein, the analytes are analyzed using various analyses, depending on what the analyte is.

For example, analysis may include DNA analysis, RNA analysis, protein analysis, tagmentation, nucleic acid amplification, nucleic acid sequencing, nucleic acid library preparation, assay for transposase accessible chromatic using sequencing (ATAC-seq), contiguity-preserving transposition (CPT-seq), single cell combinatorial indexed sequencing (SCI-seq), or single cell genome amplification, or any combination thereof.

BRIEF DESCRIPTION OF THE DRAWINGS

FIG. 5A schematically shows the general principles of ATAC-seq, and FIG. 5B outlines steps for performing single-cell ATAC-seq.

As shown in FIG. 6A, a cell nucleus is isolated, and the DNA is tagmented with a polyA tail. Tagmented DNA and mRNA are captured with a probe and purified for further analysis. FIG. 6B shows additional details of the DNA fragments used in the process of FIG. 6A.

As shown in FIG. 7A, a cell nucleus is isolated, and DNA is tagmented with a polyA tail. Tagmented DNA and mRNA are captured using biotin capture. FIG. 7B shows additional details of the DNA fragments used in the process of FIG. 7A.

DETAILED DESCRIPTION

Figure 1A:
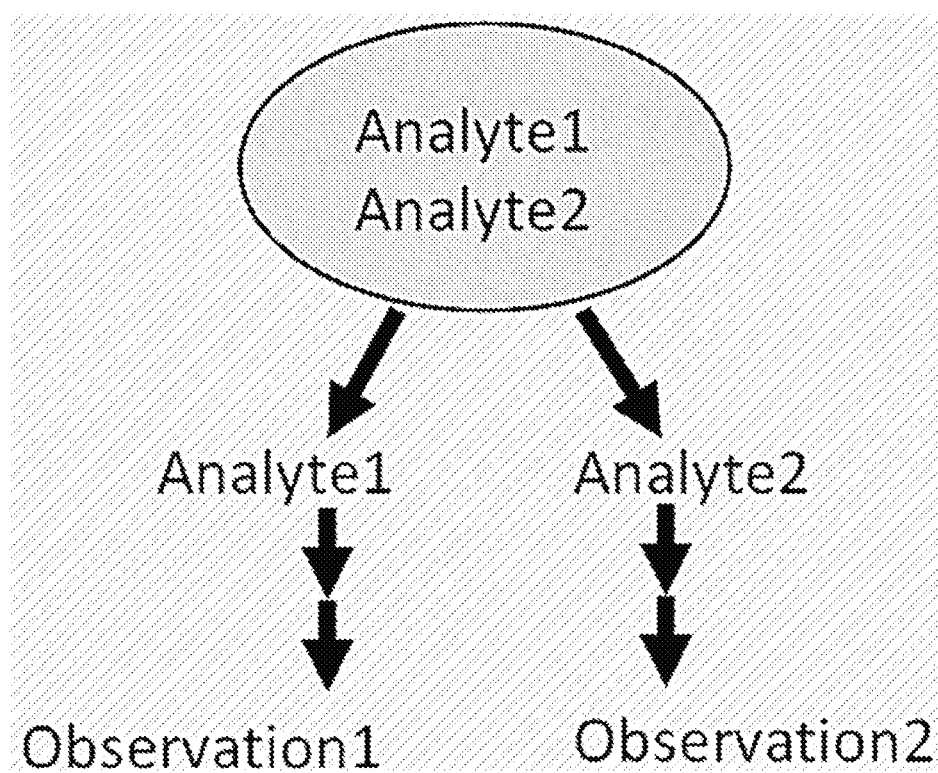
FIG. 1A is a schematic that illustrates traditional methods for analyzing multiple analytes of interest in a sample, wherein each analyte of interest is separately analyzed at two different observations.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Embodiments of the systems, methods, and compositions provided herein relate to the simultaneous analysis of multiple analytes in a single sample. In some embodiments, the multiple analytes include DNA and RNA.

Traditional methods of analyzing multiple analytes from a single sample requires separate assays, involving the use of separate reagents and steps for isolating each analyte of interest and then analyzing each analyte of interest, as shown for example in FIG. 1A. Thus, the analytes may be separately analyzed by time and/or space, for example at different times or in different compartments. For example, it may be desirable to analyze both DNA and RNA from a single sample. Traditional methods separately analyze DNA using one assay, and RNA using another assay, thereby increasing the time, cost, and consumption of resources. Further, the same sample may also include additional analytes of interest, such as protein, and the analysis of protein also requires a separate assay.

Nucleic acid libraries are useful for determining gene products or for whole genome sequencing. Different types of libraries may be generated, for example, complementary DNA (cDNA) libraries, generated from reverse-transcribed RNA or genomic DNA (gDNA) libraries, including for use in epigenomics, such as by assay for transposase accessible chromatic using sequencing (ATAC-seq), a rapid and sensitive method of integrative epigenomic analysis. Traditionally, these libraries are separately and independently generated. cDNA libraries may be useful for a number of applications, including, for example, discovery of novel genes, for studying gene function, for determining mRNA expression, or for determining alternate splicing. gDNA libraries may be useful for a number of separate applications, including, for example, determining complete genome of an organism, studying the function of regulatory sequences, or studying genetic mutations. The methods, compositions, and systems described herein enable the simultaneous generations of both cDNA and gDNA libraries.

Figure 1B:
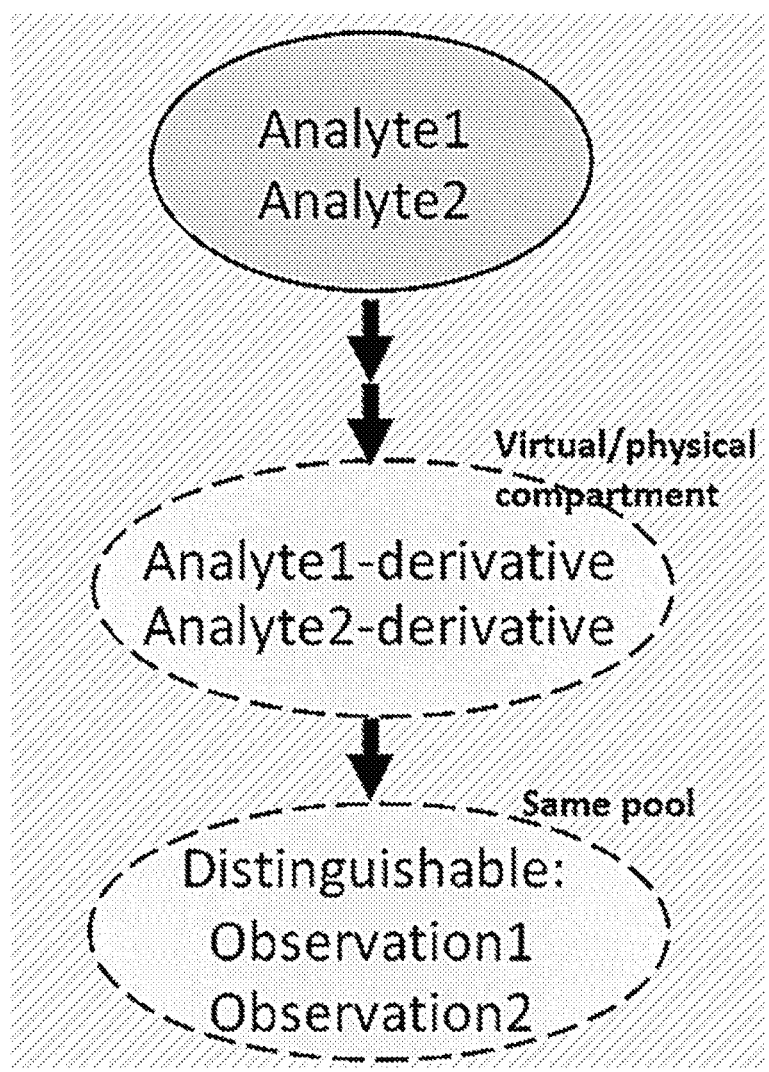
FIG. 1B is a schematic of an embodiment of a process for simultaneously measuring different analytes of interest within the same compartment.

One embodiment of the invention is a system and method to analyze multiple analytes in a single sample using a single assay, wherein each analyte of interest is analyzed simultaneously in a single compartment, for example as shown in FIG. 1B. Although FIG. 1B depicts two analytes in a sample, it is to be understood that more than two analytes of interest may be present, and each analyte of interest may be simultaneously analyzed. The systems, methods, and compositions described herein relate to the simultaneous analysis of multiple analytes in a single sample. Embodiments of the systems, methods, and compositions improve the efficiency of analysis by decreasing assay complexity, costs, and time.

Some embodiments provided herein relate to a nucleic acid library. In some embodiments, the nucleic acid library comprises a cDNA library derived from mRNA molecules and comprising nucleic acids having a first tag configured to bind to a substrate and a barcode sequence and a gDNA library derived from genomic DNA and comprising nucleic acids having a second tag configured to bind to the substrate and that differs from the first tag. In some embodiments, the nucleic acid library is generated from a population of cells, a single cell, a population of cell nuclei, or a cell nucleus. In some embodiments, the first tag is a polyA tag. In some embodiments, the second tag comprises a transposase-specific element.

In some embodiments, the method includes tagging each analyte of interest in the sample with a tag to index each analyte of interest. In some embodiments, the method further includes capturing each analyte of interest with a probe that is complementary to the tag. In some embodiments, the method further includes analyzing each analyte of interest.

In some embodiments, the method includes simultaneously analyzing DNA and RNA a sample. In some embodiments, the method includes providing a sample comprising DNA and RNA. In some embodiments, the RNA comprises a first tag. In some embodiments, the method includes differentially tagging DNA with a second tag. In some embodiments, the method includes contacting a solid support with the sample, wherein the solid support comprises a first immobilized probe for capturing the RNA and a second immobilized probe for capturing the tagged DNA. In some embodiments, the method includes simultaneously capturing DNA and RNA on the solid support. In some embodiments, the method includes analyzing DNA and RNA.

As used herein, a sample includes any sample having an analyte of interest. The sample may be a biological sample, such as a biological sample having an analyte of interest, including, for example, whole blood, serum, interstitial fluid, lymph, cerebrospinal fluid, sputum, urine, stool, milk, sweat, tears, umbilical cord, peripheral blood, bone marrow, cells or solid tissue. In some embodiments, the sample is a population of cells, a cell, a population of cell nuclei, or a cell nucleus. The sample may be obtained from a subject, wherein it is desirable to analyze one or more analyte of interest from the subject. As used herein, a "subject" refers to an animal that is the object of treatment, observation, or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

Some embodiments provided herein relate to a method of simultaneously analyzing multiple analytes of interest in a sample, wherein the analyte of interest is one or more of nucleic acid or amino acid, such as DNA, RNA, protein, or any other cellular biomolecule, or other target molecule of interest.

The sample may be a fluid or specimen obtained from an environmental source. For example, the fluid or specimen obtained from the environmental source can be obtained or derived from food products, food produce, poultry, meat, fish, beverages, dairy product, water (including wastewater), ponds, rivers, reservoirs, swimming pools, soils, food processing and/or packaging plants, agricultural places, hydrocultures (including hydroponic food farms), pharmaceutical manufacturing plants, animal colony facilities, or any combinations thereof. In some embodiments, the sample is a fluid or specimen collected or derived from a cell culture or from a microbe colony.

As used herein, "analyte", "target analyte", "analyte of interest" are used interchangeably and refer to the analyte being measured in the methods and systems disclosed herein. In some embodiments, the analyte may be a biomolecule. Non-limiting examples of biomolecules include macromolecules such as, polynucleotide (e.g., DNA or RNA), proteins, lipids, and carbohydrates. In certain instances, the analyte may be hormones, antibodies, growth factors, cytokines, enzymes, receptors (e.g., neural, hormonal, nutrient, and cell surface receptors) or their ligands, cancer markers (e.g., PSA, TNF-alpha), markers of myocardial infarction (e.g., troponin, creatine kinase, and the like), toxins, drugs (e.g., drugs of addiction), metabolic agents (e.g., including vitamins), and the like. Non-limiting embodiments of protein analytes include peptides, polypeptides, protein fragments, protein complexes, fusion proteins, recombinant proteins, phosphoproteins, glycoproteins, lipoproteins, proteins tagged with oligonucleotides, or the like. The target analyte may be a nucleic acid.

Target nucleic acids can include a sample in which the average size of a nucleic acid in the sample is less than, greater than, or equal to about 2 kb, 1 kb, 500 bp, 400 bp, 200 bp, 100 bp, 50 bp, or a range between any two of the foregoing sizes. In some embodiments, the average size of a nucleic acid in the sample is less than, greater than, or equal to about 2000 nucleotides, 1000 nucleotides, 500 nucleotides, 400 nucleotides, 200 nucleotides, 100 nucleotides, 50 nucleotides, or a range between any two of the foregoing sizes.

As used herein "polynucleotide" and "nucleic acid", may be used interchangeably, and can refer to a polymeric form of nucleotides of any length, either ribonucleotides or deoxyribonucleotides. Thus, these terms include single-, double-, or multi-stranded DNA or RNA. Examples of polynucleotides include a gene or gene fragment, whole genomic DNA, genomic DNA, epigenomic, genomic DNA fragment, exon, intron, messenger RNA (mRNA), regulatory RNA, transfer RNA, ribosomal RNA, non-coding RNA (ncRNA) such as PIWI-interacting RNA (piRNA), small interfering RNA (siRNA), and long non-coding RNA (lncRNA), small hairpin (shRNA), small nuclear RNA (snRNA), micro RNA (miRNA), small nucleolar RNA (snoRNA) and viral RNA, ribozyme, cDNA, recombinant polynucleotide, branched polynucleotide, plasmid, vector, isolated DNA of any sequence, isolated RNA of any sequence, nucleic acid probe, primer or amplified copy of any of the foregoing. A polynucleotide can include modified nucleotides, such as methylated nucleotides and nucleotide analogs including nucleotides with non-natural bases, nucleotides with modified natural bases such as aza- or deaza-purines. A polynucleotide can be composed of a specific sequence of four nucleotide bases: adenine (A); cytosine (C); guanine (G); and thymine (T). Uracil (U) can also be present, for example, as a natural replacement for thymine when the polynucleotide is RNA. Uracil can also be used in DNA. The term "nucleic acid sequence" can refer to the alphabetical representation of a polynucleotide or any nucleic acid molecule, including natural and non-natural bases.

A nucleic acid can contain phosphodiester bonds, and can include other types of backbones, comprising, for example, phosphoramide, phosphorothioate, phosphorodithioate, O-methylphosphoroamidite and peptide nucleic acid backbones and linkages. A nucleic acid can contain any combination of deoxyribo- and ribonucleotides, and any combination of bases, including uracil, adenine, thymine, cytosine, guanine, inosine, xanthanine, hypoxanthanine, isocytosine, isoguanine, and base analogs such as nitropyrrole (including 3-nitropyrrole) and nitroindole (including 5-nitroindole). In some embodiments, a nucleic acid can include at least one promiscuous base. A promiscuous base can base-pair with more than one different type of base and can be useful, for example, when included in oligonucleotide primers or inserts that are used for random hybridization in complex nucleic acid samples such as genomic DNA samples. An example of a promiscuous base includes inosine that may pair with adenine, thymine, or cytosine. Other examples include hypoxanthine, 5-nitroindole, acyclic 5-nitroindole, 4-nitropyrazole, 4-nitroimidazole and 3-nitropyrrole. Promiscuous bases that can base pair with at least two, three, four or more types of bases can be used.

As used herein, the term simultaneous refers to an action that takes place at the same time or at substantially the same time. Thus, simultaneous analysis of multiple analytes refers to analyzing multiple analytes in a single assay at the same time or substantially at the same time. Similarly, simultaneous collecting or deriving of sequenceable elements refers to collecting or deriving sequenceable elements at the same time or substantially at the same time.

As used herein, the term tag refers to a modification on the analyte or analytes of interest such that the analyte of interest can later be isolated, identified, tracked, or analyzed. Thus, a tag can identify the analyte of interest in the sample. A tag may include, for example, a poly adenylation (polyA) tag. In some embodiments, a tag can include a nucleotide sequence having a length of at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 30 nucleotides, at least 35 nucleotides, at least 40 nucleotides, at least 45 nucleotides, at least 50 nucleotides, or 50 nucleotides or greater, or a length within a range of any two of the foregoing lengths. In some embodiments, tagging is performed by tagmentation. As used herein, "tagmentation" can refer to the insertion of transposons into target nucleic acids such that the transposon cleaves the target nucleic acids, and adds adaptor sequences to the ends of the cleaved target nucleic acids. Example methods of tagmentation are disclosed in U.S. Pat. Nos. 9,115,396; 9,080,211; 9,040,256; U.S. patent application publication 2014/0194324, each of which is incorporated herein by reference in its entirety. In some embodiments, the tag is the same or different for each analyte of interest. For example, each analyte of interest may be tagged with the same tag, or may be tagged with a different tag. Differentially tagging, for example, refers to tagging one analyte of interest, such as DNA, in such a way that the tagging is different from or distinct from tagging of another analyte of interest, such as RNA. In some embodiments, the tag is different for each analyte, but the relationship of the tag is known beforehand.

Transposon based technology can be utilized for fragmenting DNA, for example, as exemplified in the workflow for NEXTERA™ XT and FLEX DNA sample preparation kits (Illumina, Inc.), wherein target nucleic acids, such as genomic DNA, are treated with transposome complexes that simultaneously fragment and tag (tagmentation) the target, thereby creating a population of fragmented nucleic acid molecules tagged with unique adaptor sequences at the ends of the fragments.

A transposition reaction is a reaction wherein one or more transposons are inserted into target nucleic acids at random sites or almost random sites. Components in a transposition reaction include a transposase (or other enzyme capable of fragmenting and tagging a nucleic acid as described herein, such as an integrase) and a transposon element that includes a double-stranded transposon end sequence that binds to the transposase (or other enzyme as described herein), and an adaptor sequence attached to one of the two transposon end sequences. One strand of the double-stranded transposon end sequence is transferred to one strand of the target nucleic acid and the complementary transposon end sequence strand is not (a non-transferred transposon sequence). The adaptor sequence can include one or more functional sequences or components (e.g., primer sequences, anchor sequences, universal sequences, spacer regions, or index tag sequences) as needed or desired.

A "transposome complex" is comprised of at least one transposase (or other enzyme as described herein) and a transposon recognition sequence. In some such systems, the transposase binds to a transposon recognition sequence to form a functional complex that is capable of catalyzing a transposition reaction. In some aspects, the transposon recognition sequence is a double-stranded transposon end sequence. The transposase binds to a transposase recognition site in a target nucleic acid and inserts the transposon recognition sequence into a target nucleic acid. In some such insertion events, one strand of the transposon recognition sequence (or end sequence) is transferred into the target nucleic acid, resulting in a cleavage event. Exemplary transposition procedures and systems that can be readily adapted for use with the transposases of the present disclosure are described, for example, in PCT Publ. No. WO10/048605, U.S. Pat. Publ. No. 2012/0301925, U.S. Pat. Publ. No. 2012/13470087, or U.S. Pat. Publ. No. 2013/0143774, each of which is incorporated herein by reference in its entirety.

Exemplary transposases that can be used with certain embodiments provided herein include (or are encoded by): Tn5 transposase (see Reznikoff et al., *Biochem. Biophys. Res. Commun.* 1999, 266, 729-734), Sleeping Beauty (SB) transposase, *Vibrio harveyi* (transposase characterized by Agilent and used in SureSelect QXT product), MuA transposase and a Mu transposase recognition site comprising R1 and R2 end sequences (Mizuuchi, K., Cell, 35: 785, 1983; Savilahti, H, et al., EMBO J., 14:4893, 1995), *Staphylococcus aureus* Tn552 (Colegio, O. et al., J. Bacteriol., 183: 2384-8, 2001; Kirby, C. et al., Mol. Microbiol., 43:173-86, 2002), Ty1 (Devine & Boeke, Nucleic Acids Res., 22:3765-72, 1994 and PCT Publ. No. WO95/23875), Transposon Tn7 (Craig, N. L., Science, 271:1512, 1996; Craig, N. L., Curr. Top. Microbiol. Immunol., 204:27-48, 1996), Tn/O and IS10 (Kleckner N. et al., Curr. Top. Microbiol. Immunol., 204: 49-82, 1996), Mariner transposase (Lampe, D. J. et al., EMBO J., 15:5470-9, 1996), Tc1 (Plasterk, R. H., Curr. Top. Microbiol. Immunol., 204:125-43, 1996), P Element (Gloor, G. B., Methods Mol. Biol., 260:97-114, 2004), Tn3 (Ichikawa & Ohtsubo, J. Biol. Chem., 265:18829-32, 1990), bacterial insertion sequences (Ohtsubo & Sekine, Curr. Top. Microbiol. Immunol. 204:1-26, 1996), retroviruses (Brown et al., Proc. Natl. Acad. Sci. USA, 86:2525-9, 1989), and retrotransposon of yeast (Boeke & Corces, Ann. Rev. Microbiol. 43:403-34, 1989). More examples include IS5, Tn10, Tn903, IS911, and engineered versions of transposase family enzymes (Zhang et al., (2009) PLoS Genet. 5:e1000689. Epub Oct. 16; Wilson C. et al. (2007) J. Microbiol. Methods 71:332-5), each of the references cited herein with respect to the transposase is incorporated herein by reference in its entirety. The methods described herein could also include combinations of transposases, and not just a single transposase.

In some embodiments, the transposase is a Tn5, MuA, or *Vibrio harveyi* transposase, or an active mutant thereof. In other embodiments, the transposase is a Tn5 transposase or an active mutant thereof. In some embodiments, the Tn5 transposase is a hyperactive Tn5 transposase (see, e.g., Reznikoff et al., PCT Publ. No. WO2001/009363, U.S. Pat. Nos. 5,925,545, 5,965,443, 7,083,980, and 7,608,434, and Goryshin and Reznikoff, J. Biol. Chem. 273:7367, 1998), or an active mutant thereof. In some aspects, the Tn5 transposase is a Tn5 transposase as described in PCT Publ. No. WO2015/160895, which is incorporated herein by reference. In some embodiments, the Tn5 transposase is a fusion protein. In some embodiments, the Tn5 transposase fusion protein comprises a fused elongation factor Ts (Tsf) tag. In some embodiments, the Tn5 transposase is a hyperactive Tn5 transposase comprising mutations at amino acids 54, 56, and 372 relative to the wild type sequence. In some embodiments, the hyperactive Tn5 transposase is a fusion protein, optionally wherein the fused protein is elongation factor Ts (Tsf). In some embodiments, the recognition site is a Tn5-type transposase recognition site (Goryshin and Reznikoff, J. Biol. Chem., 273:7367, 1998). In one embodiment, a transposase recognition site that forms a complex with a hyperactive Tn5 transposase is used (e.g., EZ-Tn5™ Transposase, Epicentre Biotechnologies, Madison, Wis.). In some embodiments, the Tn5 transposase is a wild-type Tn5 transposase.

In any of the embodiments of the methods, compositions, or systems described herein, the transposon includes a transposon end sequence. In some embodiments, the transposon end sequence is a mosaic end (ME) sequence. In some embodiments, DNA is tagged using tagmentation, wherein the DNA is tagged with a tag, and included with the tag is a transposon-specific sequence, such as an ME sequence. Thus, the DNA is differentiated from RNA in the sample based on the transposon-specific sequence.

In any of the embodiments of the methods, compositions, or systems described herein, the transposon includes an adaptor sequence. Adaptor sequences may comprise one or more functional sequences or components selected from the group consisting of primer sequences, anchor sequences, universal sequences, spacer regions, index sequences, capture sequences, barcode sequences, cleavage sequences, sequencing-related sequences, and combinations thereof. In some embodiments, an adaptor sequence comprises a primer sequence. In other embodiments, an adaptor sequence comprises a primer sequence and an index or barcode sequence. A primer sequence may also be a universal sequence. This disclosure is not limited to the type of adaptor sequences that could be used and a skilled artisan will recognize additional sequences that may be of use for library preparation and next generation sequencing. A universal sequence is a region of nucleotide sequence that is common to two or more nucleic acid fragments. Optionally, the two or more nucleic acid fragments also have regions of sequence differences. A universal sequence that may be present in different members of a plurality of nucleic acid fragments can allow for the replication or amplification of multiple different sequences using a single universal primer that is complementary to the universal sequence.

Adaptors include nucleic acids, such as single-stranded nucleic acids. Adaptors can include short nucleic acids having a length less than, greater than, or equal to about 5 nucleotides, 10 nucleotides, 20 nucleotides, 30 nucleotides, 40 nucleotides, 50 nucleotides, 60 nucleotides, 70 nucleotides, 80 nucleotides, 90 nucleotides, 100 nucleotides, or a range between any two of the foregoing sizes.

In any of the embodiments, the adaptor sequence or transposon end sequences, including A14-ME, ME, B15-ME, ME', A14, B15, and ME are provided below:

```
A14-ME:
                                         (SEQ ID NO: 1)
5'-TCGTCGGCAGCGTCAGATGTGTATAAGAGACAG-3'

B15-ME:
                                         (SEQ ID NO: 2)
5'-GTCTCGTGGGCTCGGAGATGTGTATAAGAGACAG-3'

ME':
                                         (SEQ ID NO: 3)
5'-phos-CTGTCTCTTATACACATCT-3'

A14:
                                         (SEQ ID NO: 4)
5'-TCGTCGGCAGCGTC-3'

B15:
                                         (SEQ ID NO: 5)
5'-GTCTCGTGGGCTCGG-3'

ME:
                                         (SEQ ID NO.: 6)
AGATGTGTATAAGAGACAG
```

In some embodiments, the primer sequences are includes to prepare the libraries for sequencing. In some embodiments, the primer sequence is a P5 primer sequence or a P7 primer sequence. The P5 and P7 primers are used on the surface of commercial flowcells sold by Illumina, Inc., for sequencing on various Illumina platforms. The primer sequences are described in U.S. Patent Publication No. 2011/0059865 A1, which is incorporated herein by reference in its entirety. Examples of P5 and P7 primers, which may be alkyne terminated at the 5' end, include the following:

```
P5:
                                         (SEQ ID NO. 7)
AATGATACGGCGACCACCGAGAUCTACAC

P7:
                                         (SEQ ID NO. 8)
CAAGCAGAAGACGGCATACGAG*AT
``` and derivatives or analogues thereof. In some examples, the P7 sequence includes a modified guanine at the G* position, e.g., an 8-oxo-guanine. In other examples, the * indicates that the bond between the G* and the adjacent 3' A is a phosphorothioate bond. In some examples, the P5 and/or P7 primers include unnatural linkers. Optionally, one or both of the P5 and P7 primers can include a poly T tail. The poly T tail is generally located at the 5' end of the sequence shown above, e.g., between the 5' base and a terminal alkyne unit, but in some cases can be located at the 3' end. The poly T sequence can include any number of T nucleotides, for example, from 2 to 20. While the P5 and P7 primers are given as examples, it is to be understood that any suitable primers can be used in the examples presented herein. The index sequences having the primer sequences, including the P5 and P7 primer sequences serve to add P5 and P7 for activating the library for sequencing.

As used herein the term probe refers to a capture molecule having sufficient binding properties to specifically bind to a target analyte, for example to a tag on a target analyte. For example, a probe may include a polynucleotide having sufficient complementarity to specifically hybridize to a target nucleic acid. For example, a probe may include a polyT sequence for specifically binding to a polyA tag. In another example, a probe comprises an antibody or a protein tag. A capture probe can function as an affinity-binding molecule for isolation of a target nucleic acid from other nucleic acids and/or components in a mixture. A target nucleic acid can also be specifically bound by a capture probe through intervening molecules such as linkers, adapters and other bridging nucleic acids having sufficient complementarity to specifically hybridize to both a target sequence and a capture probe.

In some embodiments, the probe further includes a barcode. A barcode identifies a target as being from a certain sample. For example, a barcode is used to identify one or more analytes as being from a common source. A barcode identifying one analyte may be the same or different from a barcode identifying a different analyte. So long as the relationship between the barcodes is known, the barcodes may be used to identify the analytes as being from a common source.

In some embodiments, a barcode can include a nucleic acid sequence that can be used to identify a polynucleotide within an array. The barcode can include a unique nucleotide sequence that is distinguishable from other barcodes. It can also be distinguishable from other nucleotide sequences within the polynucleotides and target nucleic acids by the barcode's sequence, and also by the barcode's location within the polynucleotide, for example by its location 5' of the primer binding site. For example, in some embodiments, the sequence of a barcode may be present more than once in a plurality of nucleic acids; however, the barcode which is located 5' of the primer binding site can be detected. A barcode can be of any desired sequence length sufficient to be unique nucleotide sequence within a plurality of barcodes in a population and/or within a plurality of polynucleotides and target nucleic acids that are being analyzed or interrogated. In some embodiments, a barcode is a nucleic acid or region within a polynucleotide ranging from about 1-30 nucleotides or greater. For example, a barcode can have a length of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides, or greater. In some embodiments, a barcode can be 35, 40, 45 or 50 nucleotides or longer. In some embodiments, a barcode can distinguish a polynucleotide from another polynucleotide in an array, such that each barcode is different from another barcode. In some embodiments, a barcode can distinguish a population of polynucleotides from another population of polynucleotides in an array, such that a set of barcode is different from another set of barcodes.

In some embodiments, a barcode is directly inserted using transposition. In such embodiments, no binding event to a solid support is needed. Thus, in any of the embodiments provided herein the analytes of interest are simultaneously analyzed with or without a solid support.

In some embodiments, the probe may be immobilized on a solid support. A solid support may include, for example, an etched surface, a well, a covered well, an array, a flowcell device, a microfluidic channel, a bead, a magnetic bead, a column, a droplet, or a microparticle. In such embodiments, the analyte of interest is bound by the immobilized probe to a solid support, where the analyte of interest undergoes further processing or analysis on a solid support. In some embodiments, the immobilized probe and the solid support are used in solution. For example, the immobilized support may be a bead, and the probe, attached to the bead, are soluble in solution for capture of analyte of interest, such as DNA and RNA, in solution. In such embodiments, the tagged analyte of interest binds to the probe in solution, and the tagged analyte of interest is barcoded in solution. The barcoded analyte of interest may undergo further processing or analysis in solution, or may be pulled down using a pull down assay, including through the use of magnetic beads.

The term flowcell as used herein refers to a chamber comprising a solid surface across which one or more fluid reagents can be flowed. Examples of flowcells and related fluidic systems and detection platforms that can be readily used in the methods of the present disclosure include, for example, microfluidic devices, microstructures, microwells, microtitre plates, or the like, and are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

As used herein, "array" can refer to a population of different microfeatures, such as microfeatures comprising polynucleotides, which are associated or attached with a surface such that the different microfeatures can be differentiated from each other according to relative location. An individual feature of an array can include a single copy of a microfeature or multiple copies of the microfeature can be present as a population of microfeatures at an individual feature of the array. The population of microfeatures at each feature typically is homogenous, having a single species of microfeature. Thus, multiple copies of a single nucleic acid sequence can be present at a feature, for example, on multiple nucleic acid molecules having the same sequence.

In some embodiments, a heterogeneous population of microfeatures can be present at a feature. In some embodiments, a feature can include only a single microfeature species. In some embodiments, a feature can include a plurality of different microfeature species, such as a mixture of nucleic acids having different sequences. Neighboring features of an array can be discrete from one another. Features can be adjacent to each other or separated by a gap. In embodiments where features are spaced apart, neighboring sites can be separated, for example, by a distance of less than 100 µm, 50 µm, 10 µm, 5 µm, 1 µm, 0.5 µm, 100 nm, 50 nm, 10 nm, 5 nm, 1 nm, 0.5 nm or any distance within a range of any two of the foregoing distances. The layout of features on an array can also be understood in terms of center-to-center distances between neighboring features. An array useful in the invention can have neighboring features with center-to-center spacing of less than about 100 µm, 50 µm, 10 µm, 5 µm, 1 µm, 0.5 µm, 100 nm, 50 nm, 10 nm, 5 nm, 1 nm, 0.5 nm or any distance within a range of any two of the foregoing distances. In some embodiments, the distance values described herein can represent an average distance between neighboring features of an array. As such, not all neighboring features need to fall in the specified range unless specifically indicated to the contrary, for example, by a specific statement that the distance constitutes a threshold distance between all neighboring features of an array. Embodiments can include arrays having features at a variety of densities. Example ranges of densities for certain embodiments include from about 10,000,000 features/cm$^2$ to about 2,000,000,000 features/cm$^2$; from about 100,000,000 features/cm$^2$ to about 1,000,000,000 features/cm$^2$; from about 100,000 features/cm$^2$ to about 10,000,000 features/cm$^2$; from about 1,000,000 features/cm$^2$ to about 5,000,000 features/cm$^2$; from about 10,000 features/cm$^2$ to about 100,000 features/cm$^2$; from about 20,000 features/cm$^2$ to about 50,000 features/cm$^2$; from about 1,000 features/cm$^2$ to about 5,000 features/cm$^2$, or any density within a range of any two of the foregoing densities.

As used herein, "surface" can refer to a part of a substrate or support structure that is accessible to contact with reagents, beads or analytes. The surface can be substantially flat or planar. Alternatively, the surface can be rounded or contoured. Example contours that can be included on a surface are wells, depressions, pillars, ridges, channels or the like. Example materials that can be used as a substrate or support structure include glass such as modified or functionalized glass; plastic such as acrylic, polystyrene or a copolymer of styrene and another material, polypropylene, polyethylene, polybutylene, polyurethane or TEFLON; polysaccharides or cross-linked polysaccharides such as agarose or sepharose; nylon; nitrocellulose; resin; silica or silica-based materials including silicon and modified silicon; carbon-fiber; metal; inorganic glass; optical fiber bundle, or a variety of other polymers. A single material or mixture of several different materials can form a surface useful in the invention. In some embodiments, a surface comprises wells.

As used herein, "bead" can refer to a small body made of a rigid or semi-rigid material. The body can have a shape characterized, for example, as a sphere, oval, microsphere, or other recognized particle shape whether having regular or irregular dimensions. Example materials that are useful for beads include glass such as modified or functionalized glass; plastic such as acrylic, polystyrene or a copolymer of styrene and another material, polypropylene, polyethylene, polybutylene, polyurethane or TEFLON; polysaccharides or cross-linked polysaccharides such as agarose or Sepharose; nylon; nitrocellulose; resin; silica or silica-based materials including silicon and modified silicon; carbon-fiber; metal; inorganic glass; optical fiber bundle, or a variety of other polymers. Example beads include controlled pore glass beads, paramagnetic beads, thoria sol, Sepharose beads, nanocrystals and others known in the art. Beads can be made of biological or non-biological materials. Magnetic beads are particularly useful due to the ease of manipulation of magnetic beads using magnets. Beads used in certain embodiments can have a diameter, width or length from 0.1 μm to 100 μm. Bead size can be selected to have a reduced size, and hence have increased density, whilst maintaining sufficient signal to analyze the features.

As used herein, "hybridization", "hybridizing" or grammatical equivalent thereof, can refer to a reaction in which one or more polynucleotides react to form a complex that is formed at least in part via hydrogen bonding between the bases of the nucleotide residues. The hydrogen bonding can occur by Watson-Crick base pairing, Hoogstein binding, or in any other sequence-specific manner. The complex can have two strands forming a duplex structure, three or more strands forming a multi-stranded complex, a single self-hybridizing strand, or any combination of thereof. The strands can also be cross-linked or otherwise joined by forces in addition to hydrogen bonding.

As used herein, "extending", "extension" or any grammatical equivalents thereof can refer to the addition of dNTPs to a primer, polynucleotide or other nucleic acid molecule by an extension enzyme such as a polymerase. For example, in some embodiments disclosed herein, the resulting extended primer includes sequence information of a nucleic acid. While some embodiments are discussed as performing extension using a polymerase such as a DNA polymerase, or a reverse transcriptase, extension can be performed in any other manner well known in the art. For example, extension can be performed by ligating oligonucleotides together, such as oligonucleotides that have hybridized to a strand of interest.

As used herein, "ligation" or "ligating" or other grammatical equivalents thereof can refer to the joining of two nucleotide strands by a phosphodiester bond. Ligation may include chemical ligation. Such a reaction can be catalyzed by a ligase. A ligase refers to a class of enzymes that catalyzes this reaction with the hydrolysis of ATP or a similar triphosphate.

Some embodiments provided herein relate to simultaneously analyzing multiple analytes in a sample using a single assay, wherein the multiple analytes include DNA and RNA. In some embodiments, the target DNA and target RNA are modified by tagging. Thus, in some embodiments, the method includes modifying the DNA in the sample with a first tag and modifying the RNA in the sample with a second tag. In some embodiments, the method includes capturing the modified DNA with a first probe complementary to the first tag and capturing the modified RNA with a second probe complementary to the second tag. In some embodiments, the method includes analyzing the captured DNA and RNA. As used herein, the terms "first tag" and "second tag" do not refer to any particular timing or sequence of tagging events. Rather, the terms or merely used for delineating that a first analyte includes one tag, termed for example as a first tag, and that a second analyte includes another tag, termed for example as a second tag. In any of the embodiments described herein, the first and second tags can be the same or different. Whereas a barcode identifies the analytes as being from a common source, a tag identifies the analyte as a certain type, for example, as DNA or RNA.

In some embodiments, the method further includes simultaneously analyzing an additional analyte of interest, in addition to the DNA and RNA, for example, analyzing a protein. In such embodiments, the additional analyte of interest, such as a protein is modified with an additional tag.

In some embodiments, the first and second tags (or additional tags where relevant) are different. In some embodiments, the first and second tags (or additional tags where relevant) are the same. In some embodiments, the first and second tag further comprise a substrate recognition sequence. A substrate recognition sequence is a sequence that recognizes a substrate and binds thereto, thereby immobilizing the tag. In some embodiments, the substrate recognition sequence of the first tag is the same as the substrate recognition sequence of the second tag.

Figure 2:
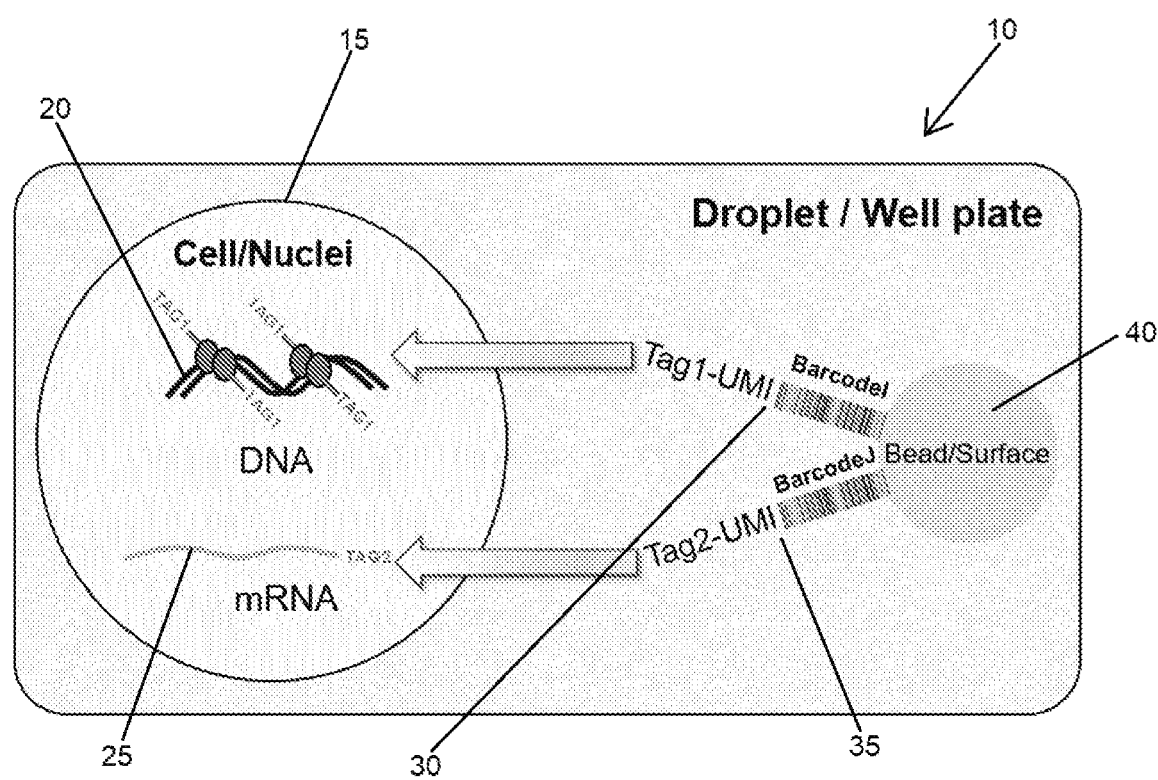
FIG. 2 is a schematic diagram depicting an embodiment of a co-assay using different tags for binding to DNA and RNA. The different tags are shown as being introduced into a single cell or nucleus having the RNA or DNA. The single cell or nucleus is encapsulated within a droplet or separated on a well of a plate. A barcode is immobilized on a surface or added in solution, and captures the DNA and RNA via the tags.

In some embodiments, DNA is tagged via tagmentation process, as shown in FIG. 2. In the embodiment of FIG. 2, a well plate 10 is shown having an isolated single cell or nucleus 15. The nucleus 15 includes DNA 20 and mRNA 25 within the nucleus 15. The single cell or nucleus 15 can be encapsulated in a droplet or separated in individual wells for analysis. The DNA 20 is shown as being tagged with TAG1, which can have been derived via a tagmentation or other tagging process, such as reverse transcription, ligation, or other means for tagging DNA. In the embodiment of FIG. 2, the mRNA 25 is tagged with TAG2. FIG. 2 also depicts probes 30, 35, which are immobilized on a solid support 40, which can be a bead or other surface. The probe 30 specific for the DNA 20 includes a TAG1 capture element, which is a capture element that specifically binds to TAG1 on the DNA 20. The probe 35 specific for the mRNA 25 includes a TAG2 capture element, which is a capture element that specifically binds to TAG2 on the mRNA 25. Each probe also includes a barcode, thereby allowing indexing of the analytes of interest, in this case, the DNA and mRNA.

Figure 3:
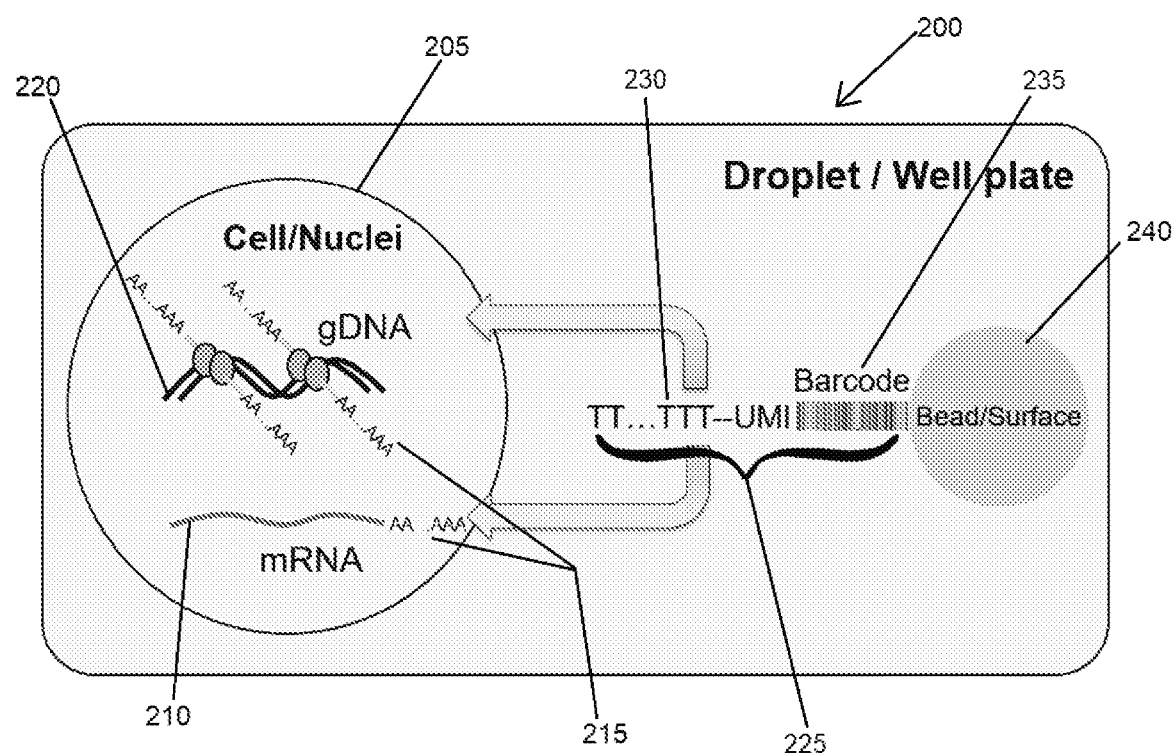
FIG. 3 is a schematic diagram depicting an embodiment of a co-assay using the same tag for binding to DNA and RNA. DNA is first fragmented by a transposome to contain a polyA tail. Both DNA fragments and mRNA are indexed using polyT oligonucleotides with a barcode immobilized on a surface or in solution. The transposition reaction performed on the DNA allows the DNA to be distinguished from the RNA by virtue of an internal transposon specific sequence.

In some embodiments, the mRNA, which includes a polyA tail, is not tagged. For example, in the embodiment shown in FIG. 3, a well plate 200 has a nuclei 205 that includes a mRNA 210 having a polyA tail 215, but is not otherwise tagged. In the embodiment of FIG. 3, gDNA 220 is tagged with a polyA tail 215. Following tagging of the gDNA 220, both the gDNA 220 and the mRNA 210 include a polyA tail 215. gDNA 220 may be tagged with a polyA tail 215 using tagmentation, for example. As shown in FIG. 3, gDNA 220 having a polyA tail 215 and mRNA 210 also having a polyA tail 215 may be captured with the same probe 225 containing a polyT capture element 230. The probe 225 is immobilized on a solid support 240. Thus, the gDNA 220 and the mRNA 210 are processed simultaneously and assigned the same barcodes 235. The gDNA 220 may be distinguished from the mRNA 210 based on a transposon-specific sequence that was incorporated during the tagmentation process. This concept is further detailed with reference to FIG. 4.

Figure 4:
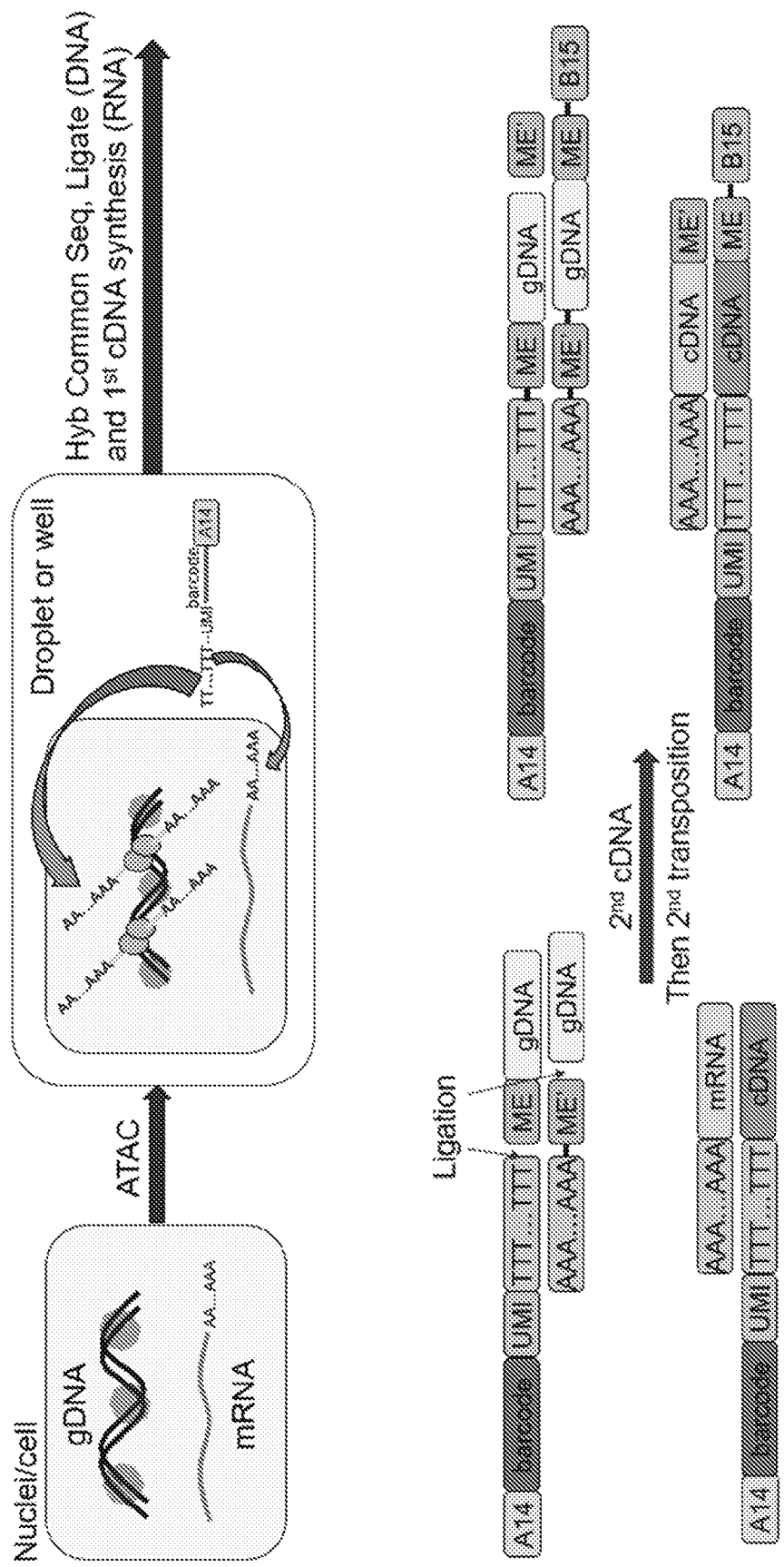
FIG. 4 is a schematic diagram depicting an embodiment of process for introducing a polyA transposon into genomic DNA by transposition. The nucleus/cell is encapsulated with the indexed oligonucleotide having a polyT tail. The indexed oligonucleotide is hybridized and ligated to a transposed gDNA fragment, and then hybridized with mRNA to generate a first cDNA. After a second cDNA synthesis, the double stranded cDNA and gDNA are transposed again to add a PCR adapter on the other end. The fragments are then amplified by PCR.

FIG. 4 depicts an exemplary method of simultaneously analyzing both gDNA and mRNA in a single sample. In this embodiment, a polyA transposon is introduced into genomic DNA by transposition. The nuclei/cell is encapsulated with the indexed probe having a polyT tail. The indexed probe is hybridized then ligated to transposed gDNA fragment, and is hybridized with mRNA. This generates a first cDNA. Following transposition, the gDNA includes an ME sequence, a tagmentation-specific sequence. After second cDNA synthesis, the double stranded cDNA and gDNA are transposed again to incorporate a PCR adapter. The fragments are then prepared for PCR amplification.

As used herein, the term "reagent" describes an agent or a mixture of two or more agents useful for reacting with, interacting with, diluting, or adding to a sample, and may include agents used in assays described herein, including agents for lysis, nucleic acid analysis, nucleic acid amplification reactions, protein analysis, tagmentation reactions, ATAC-seq, CPT-seq, or SCI-seq reactions, or other assays. Thus, reagents may include, for example, buffers, chemicals, enzymes, polymerase, primers having a size of less than 50 base pairs, template nucleic acids, nucleotides, labels, dyes, or nucleases. In some embodiments, the reagent includes lysozyme, proteinase K, random hexamers, polymerase (for example, Φ29 DNA polymerase, Taq polymerase, Bsu polymerase), transposase (for example, Tn5), primers (for example, P5 and P7 adaptor sequences), ligase, catalyzing enzyme, deoxynucleotide triphosphates, buffers, or divalent cations.

In some embodiments, a sample includes a single cell, and the single cell is fixed. In some embodiments, the cells can be fixed with a fixative. As used herein, a fixative generally refers to an agent that can fix cells. For example, fixed cells can stabilize protein complexes, nucleic acid complexes, or protein-nucleic acid complexes in the cell. Suitable fixatives and cross-linkers can include, alcohol or aldehyde based fixatives, formaldehyde, glutaraldehyde, ethanol-based fixatives, methanol-based fixatives, acetone, acetic acid, osmium tetraoxide, potassium dichromate, chromic acid, potassium permanganate, mercurials, picrates, formalin, paraformaldehyde, amine-reactive NHS-ester crosslinkers such as bis [sulfosuccinimidyl] suberate (BS3), 3,3'-dithiobis [sulfosuccinimidylpropionate] (DTS SP), ethylene glycol bis[sulfosuccinimidylsuccinate] (sulfo-EGS), disuccinimidyl glutarate (DSG), dithiobis[succinimidyl propionate] (DSP), disuccinimidyl suberate (DSS), ethylene glycol bis [succinimidylsuccinate] (EGS), NHS-ester/diazirine crosslinkers such as NHS-diazirine, NHS-LC-diazirine, NHS-SS-diazirine, sulfo-NHS-diazirine, sulfo-NHS-LC-diazirine, and sulfo-NHS-SS-diazirine. In some embodiments, fixing a cell preserves the internal state of the cell thereby preventing modification of the cell during subsequent analysis or during performance of an assay.

In some embodiments, the sample includes a nucleic acid source, such as a single cell, a single nucleus, or a population of cells or population of nuclei, and the single cell, single nucleus, population of cells, or population of nuclei is encapsulated within a droplet. In some embodiments, the cell is fixed prior to encapsulation. As used herein, a droplet may include a hydrogel bead, which is a bead for encapsulating a single cell, and composed of a hydrogel composition. In some embodiments, the droplet is a homogeneous droplet of hydrogel material or is a hollow droplet having a polymer hydrogel shell. Whether homogenous or hollow, a droplet may be capable of encapsulating a single cell. As used herein, the term "hydrogel" refers to a substance formed when an organic polymer (natural or synthetic) is cross-linked via covalent, ionic, or hydrogen bonds to create a three-dimensional open-lattice structure that entraps water molecules to form a gel. In some embodiments, the hydrogel may be a biocompatible hydrogel. As used herein, the term "biocompatible hydrogel" refers to a polymer that forms a gel that is not toxic to living cells and allows sufficient diffusion of oxygen and nutrients to entrapped cells to maintain viability. In some embodiments, the hydrogel material includes alginate, acrylamide, or poly-ethylene glycol (PEG), PEG-acrylate, PEG-amine, PEG-carboxylate, PEG-dithiol, PEG-epoxide, PEG-isocyanate, PEG-maleimide, polyacrylic acid (PAA), poly(methyl methacrylate) (PMMA), polystyrene (PS), polystyrene sulfonate (PSS), polyvinylpyrrolidone (PVPON), N,N'-bis(acryloyl)cystamine, polypropylene oxide (PPO), poly(hydroxyethyl methacrylate) (PHEMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, heparin, alginate sulfate, dextran sulfate, hyaluronan, pectin, carrageenan, gelatin, chitosan, cellulose, collagen, bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations or mixtures thereof. In some embodiments, the hydrogel is an alginate, acrylamide, or PEG based material. In some embodiments, the hydrogel is a PEG based material with acrylate-dithiol, epoxide-amine reaction chemistries. In some embodiments, the hydrogel forms a polymer shell that includes PEG-maleimide/dithiol oil, PEG-epoxide/amine oil, PEG-epoxide/PEG-amine, or PEG-dithiol/PEG-acrylate. In some embodiments, the hydrogel material is selected in order to avoid generation of free radicals that have the potential to damage intracellular biomolecules. In some embodiments, the hydrogel polymer includes 60-90% fluid, such as water, and 10-30% polymer. In certain embodiments, the water content of hydrogel is about 70-80%. As used herein, the term "about" or "approximately", when modifying a numerical value, refers to variations that can occur in the numerical value. For example, variations can occur through differences in the manufacture of a particular substrate or component. In one embodiment, the term "about" means within 1%, 5%, or up to 10% of the recited numerical value.

Hydrogels may be prepared by cross-linking hydrophilic biopolymers or synthetic polymers. Thus, in some embodiments, the hydrogel may include a crosslinker. As used herein, the term "crosslinker" refers to a molecule that can form a three-dimensional network when reacted with the appropriate base monomers. Examples of the hydrogel polymers, which may include one or more crosslinkers, include but are not limited to, hyaluronans, chitosans, agar, heparin, sulfate, cellulose, alginates (including alginate sulfate), collagen, dextrans (including dextran sulfate), pectin, carrageenan, polylysine, gelatins (including gelatin type A), agarose, (meth)acrylate-oligolactide-PEO-oligolactide-(meth)acrylate, PEO-PPO-PEO copolymers (Pluronics), poly(phosphazene), poly(methacrylates), poly(N-vinylpyrrolidone), PL(G)A-PEO-PL(G)A copolymers, poly(ethylene imine), polyethylene glycol (PEG)-thiol, PEG-acrylate, acrylamide, N,N'-bis(acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations thereof. Thus, for example, a combination may include a polymer and a crosslinker, for example polyethylene glycol (PEG)-thiol/PEG-acrylate, acrylamide/N,N'-bis(acryloyl)cystamine (BACy), or PEG/polypropylene oxide (PPO). In some embodiments, the polymer shell includes a four-arm polyethylene glycol (PEG). In some embodiments, the four-arm polyethylene glycol (PEG) is selected from the group consisting of PEG-acrylate, PEG-amine, PEG-carboxylate, PEG-dithiol, PEG-epoxide, PEG-isocyanate, and PEG-maleimide In some embodiments, the crosslinker is an instantaneous crosslinker or a slow crosslinker. An instantaneous crosslinker is a crosslinker that instantly crosslinks the hydrogel polymer, and is referred to herein as click chemistry. Instantaneous crosslinkers may include dithiol oil+PEG-maleimide or PEG epoxide+amine oil. A slow crosslinker is a crosslinker that slowly crosslinks the hydrogel polymer, and may include PEG-epoxide+PEG-amine or PEG-dithiol+PEG-acrylate. A slow crosslinker may take more than several hours to crosslink, for example more than 2, 3, 4, 5, 6, 7, 8, 9, 10, 11, or 12 hours to crosslink. In some embodiments provided herein, droplets are formulated by an instantaneous crosslinker, and thereby preserve the cell state better compared to a slow crosslinker. Without wishing to be bound by theory, cells may possible undergo physiological changes by intracellular signaling mechanisms during longer crosslinking times.

In some embodiments, a crosslinker forms a disulfide bond in the hydrogel polymer, thereby linking hydrogel polymers. In some embodiments, the hydrogel polymers form a hydrogel matrix having pores (for example, a porous hydrogel matrix). These pores are capable of retaining sufficiently large particles, such as a single cell or nucleic acids extracted therefrom within the droplet, but allow other materials, such as reagents, to pass through the pores, thereby passing in and out of the droplets. In some embodiments, the pore size of the droplets is finely tuned by varying the ratio of the concentration of polymer to the concentration of crosslinker. In some embodiments, the ratio of polymer to crosslinker is 30:1, 25:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:15, 1:20, or 1:30, or a ratio within a range defined by any two of the aforementioned ratios. In some embodiments, additional functions such as DNA primer, or charged chemical groups can be grafted to polymer matrix to meet the requirements of different applications.

As used herein, the term "porosity" means the fractional volume (dimension-less) of a hydrogel that is composed of open space, for example, pores or other openings. Therefore, porosity measures void spaces in a material and is a fraction of volume of voids over the total volume, as a percentage between 0 and 100% (or between 0 and 1). Porosity of the hydrogel may range from 0.5 to 0.99, from about 0.75 to about 0.99, or from about 0.8 to about 0.95.

In some embodiments, the droplet can have any pore size that allows for sufficient diffusion of reagents while concomitantly retaining the single cell or nucleic acids extracted therefrom. As used herein, the term "pore size" refers to a diameter or an effective diameter of a cross-section of the pores. The term "pore size" can also refer to an average diameter or an average effective diameter of a cross-section of the pores, based on the measurements of a plurality of pores. The effective diameter of a cross-section that is not circular equals the diameter of a circular cross-section that has the same cross-sectional area as that of the non-circular cross-section. In some embodiments, the hydrogel can be swollen when the hydrogel is hydrated. The sizes of the pores size can then change depending on the water content in the hydrogel. In some embodiments, the pores of the hydrogel can have a pore of sufficient size to retain the encapsulated cell within the hydrogel but allow reagents to pass through. In some embodiments, the interior of the droplet is an aqueous environment. In some embodiments, the single cell disposed within the droplet is free from interaction with the polymer shell of the droplet and/or is not in contact with the polymer shell. In some embodiments, a polymer shell is formed around a cell, and the cell is in contact with the polymer shell due to the polymer shell being brought to the cell surface due to passive adsorption or in a targeted manner, such as by being attached to an antibody or other specific binding molecule.

In some embodiments, the droplet is of a sufficient size to encapsulate a single cell. In some embodiments, the droplet has a diameter of about 20 μm to about 200 μm, such as 20, 30, 40, 50, 60, 70, 80, 90, 100, 110, 120, 130, 140, 150, 160, 170, 180, 190, or 200 μm, or a diameter within a range defined by any two of the aforementioned values. The size of the droplet may change due to environmental factors. In some embodiments, the droplets expand when they are separated from continuous oil phase and immersed in an aqueous phase. In some embodiments, expansion of the droplet increases the efficiency of performing assays on the genetic material inside the encapsulated cells. In some embodiments, expansion of the droplet creates a larger environment for indexed inserts to be amplified during PCR, which may otherwise be restricted in current cell based assays.

In some embodiments, a droplet is prepared by dynamic means, such as by vortex assisted emulsion, microfluidic droplet generation, or valve based microfluidics. In some embodiments, the droplets are formulated in a uniform size distribution. In some embodiments, the size of the droplets is finely tuned by adjusting the size of the microfluidic device, the size of the one or more channels, or the flow rate through the microfluidic channels. In some embodiments, the resulting droplet has a diameter ranging from 20 to 200 μm, for example, 20, 25, 30, 35, 40, 45, 50, 55, 60, 65, 70, 75, 80, 85, 90, 95, 100, 110, 120, 130, 140, 150, 160, 170, 180, 190, or 200 μm, or a diameter within a range defined by any two of the aforementioned values.

In some embodiments, analyzing one or more analytes may include various analyses, depending on what the analyte is. For example, analyzing may include DNA analysis, RNA analysis, protein analysis, tagmentation, nucleic acid amplification, nucleic acid sequencing, nucleic acid library preparation, assay for transposase accessible chromatic using sequencing (ATAC-seq), contiguity-preserving transposition (CPT-seq), single cell combinatorial indexed sequencing (SCI-seq), or single cell genome amplification, or any combination thereof.

DNA analysis refers to any technique used to amplify, sequence, or otherwise analyze DNA. DNA amplification can be accomplished using PCR techniques or pyrosequencing. DNA analysis may also comprise non-targeted, non-PCR based DNA sequencing (e.g., metagenomics) techniques. As a non-limiting example, DNA analysis may include sequencing the hyper-variable region of the 16S rDNA (ribosomal DNA) and using the sequencing for species identification via DNA.

RNA analysis refers to any technique used to amplify, sequence, or otherwise analyze RNA. The same techniques used to analyze DNA can be used to amplify and sequence RNA. RNA, which is less stable than DNA is the translation of DNA in response to a stimuli. Therefore, RNA analysis may provide a more accurate picture of the metabolically active members of the community and may be used to provide information about the community function of organisms in a sample. Further, simultaneous analysis of both DNA and RNA may be beneficial to efficiently determination of both DNA and RNA related interrogations. Nucleic acid sequencing refers to use of sequencing to determine the order of nucleotides in a sequence of a nucleic acid molecule, such as DNA or RNA.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

The terms "next-generation sequencing" or "high-throughput sequencing" or "NGS" generally refers to high throughput sequencing technologies, including, but not limited to, massively parallel signature sequencing, high throughput sequencing, sequencing by ligation (e.g., SOLiD sequencing), proton ion semiconductor sequencing, DNA nanoball sequencing, single molecule sequencing, and nanopore sequencing and may refer to the parallelized sequencing-by-synthesis or sequencing-by-ligation platforms currently employed by Illumina, Life Technologies, or Roche, etc. Next-generation sequencing methods may also include nanopore sequencing methods or electronic-detection based methods such as Ion Torrent technology commercialized by Life Technologies or single molecule fluorescence-based method commercialized by Pacific Biosciences.

Protein analysis refers to the study of proteins, and may include proteomic analysis, determination of post-translational modification of proteins of interest, determination of protein expression levels, or determination of protein interactions with other molecules, including with other proteins or with nucleic acids.

As used herein, the term "tagmentation" refers to the modification of DNA by a transposome complex comprising transposase enzyme complexed with adaptors comprising transposon end sequence. Tagmentation results in the simultaneous fragmentation of the DNA and ligation of the adaptors to the 5' ends of both strands of duplex fragments. Following a purification step to remove the transposase enzyme, additional sequences can be added to the ends of the adapted fragments, for example by PCR, ligation, or any other suitable methodology known to those of skill in the art.

Figure 5A:
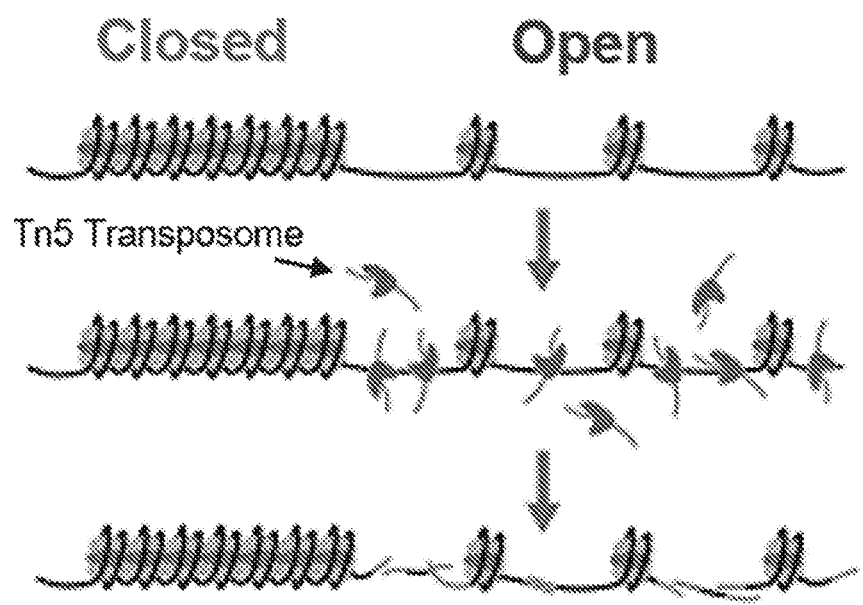
FIGS. 5A-5B schematically depict an assay for transposase accessible chromatic using sequencing (ATAC-seq).

An assay for transposase accessible chromatic using sequencing (ATAC-seq) refers to a rapid and sensitive method of integrative epigenomic analysis. ATAC-seq captures open chromatin sites and reveals interplay between genomic locations of open chromatin, DNA binding proteins, individual nucleosomes, and higher-order compaction at regulatory regions with nucleotide resolution. Classes of DNA binding factor that strictly avoid, can tolerate, or tend to overlap with nucleosomes have been discovered. Using ATAC-seq, the serial daily epigenomes of resting human T cells was measured and evaluated from a pro band via standard blood draws, demonstrating the feasibility of reading personal epigenomes in clinical timescales for monitoring health and disease. More specifically, ATAC-seq may be performed by treating chromatin from a single cell with an insertional enzyme complex to produce tagged fragments of genomic DNA. In this step, the chromatin is tagmented (for example, fragmented and tagged in the same reaction) using an insertional enzyme such as Tn5 or MuA that cleaves the genomic DNA in open regions in the chromatin and adds adaptors to both ends of the fragments. ATAC-seq allows for transposition only in open chromatin states, as outlined in FIG. 5A, and is generally described in Buenrostro et al. (Nature Methods, 2013, 10, 1213-1218), which is incorporated by reference herein in its entirety.

In any of the embodiments of the methods, compositions, or systems described herein, ATAC-seq may be performed on a single cell or in bulk. Single cell ATAC-seq allows for single cell epigenetic analysis, and may be performed in compartments, for example, by encapsulating a single cell or single nucleus within a droplet or bead. As used herein, the term compartment refers to either a physical or a virtual designation of a confined space wherein a reaction can take place. For example, a compartment can be a bead, a droplet, a well, or other physical parameter that defines an area wherein a components may be retained, for example, wherein a single cell can be subjected to experimentation and analysis. The term co-compartmentalized refers to being within a single compartment. For example, when two analytes are said to be co-compartmentalized, the analytes are both within the same compartment. Reaction products that are co-compartmentalized refers to products that are placed within the same compartment or that were prepared in the same compartment (for example, prepared in a single environment under the same reaction conditions).

Encapsulation of a single cell or single nucleus within a bead or droplet may be performed by partitioning the single cell or nucleus within a bead. Upon encapsulation, the single cell is subjected to ATAC-seq, as outlined in FIG. 5B. In single cell ATAC-seq, cells (or nuclei) may be individually compartmentalized, tagmented, and analyzed. This allows for contiguity preserving transposition (CPT-seq), as it ensures that all DNA or libraries from a single cell is encapsulated in a single droplet. Normally transposition inserts adapters and fragments the DNA after removal of the transposase. Fragmentation thereby scrambles reads from various cells into a droplet, such that single cell resolution cannot be obtained. In contrast, the methods provided herein enable the transposase to hold all the individual DNA/library fragments together, allowing all materials from a single cell to be moved into a single droplet. All fragments from a cell in a single droplet are then indexable through PCR using barcoded primers (from a bead loaded into the droplet). CPT-seq is generally described in Amini et al. (Nat Genet, 2014, 46, 1343-1349), which is incorporated by reference herein in its entirety. In addition, in some embodiments, single cell ATAC-seq can be used for combinatorial indexing. Combinatorial or split and pool indexing can be used to load multiple cells in the same well or droplet while maintaining single cell/single nucleus resolution. In some embodiments, the index can be used for sample identification, experimental condition, or for the same cells. Combinatorial indexing may be used to increase droplet utilization and cell throughput, and may be used with singe cells or nuclei.

In some cases, the conditions may be adjusted to obtain a desirable level of insertion in the chromatin (e.g., an insertion that occurs, on average, every 50 to 200 base pairs in open regions). The chromatin used in the method may be made by any suitable method. In some embodiments, nuclei may be isolated, lysed, and the chromatin may be further purified, e.g., from the nuclear envelope. In other embodiments, the chromatin may be isolated by contacting isolated nuclei with the reaction buffer. In these embodiments, the isolated nuclei may lyse when it makes contact with the reaction buffer (which comprises insertional enzyme complexes and other necessary reagents), which allows the insertional enzyme complexes access to the chromatin. In these embodiments, the method may comprise isolating nuclei from a population of cells; and combining the isolated nuclei with the transposase and adaptors, wherein the combining results in both lysis of the nuclei to release said chromatin and production of the adaptor-tagged fragments of genomic DNA. The chromatin does not require cross-linking as in other methods (e.g., ChIP-SEQ methods).

After the chromatin has been fragmented and tagged to produce tagged fragments of genomic DNA, at least some of the adaptor tagged fragments are sequenced to produce a plurality of sequence reads. The fragments may be sequenced using any suitable method. For example, the fragments may be sequenced using Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al. (Nature 2005 437: 376-80); Ronaghi et al. (Analytical Biochemistry 1996 242: 84-9); Shendure et al. (Science 2005 309: 1728-32); Imelfort et al. (Brief Bioinform. 2009 10:609-18); Fox et al. (Methods Mol Biol. 2009; 553:79-108); Appleby et al. (Methods Mol Biol. 2009; 513:19-39) and Morozova et al. (Genomics. 2008 92:255-64), which are incorporated by reference herein for the general descriptions of the methods and the particular steps of the methods, including all starting products, methods for library preparation, reagents, and final products for each of the steps. As would be apparent, forward and reverse sequencing primer sites that are compatible with a selected next generation sequencing platform can be added to the ends of the fragments during the amplification step. In certain embodiments, the fragments may be amplified using PCR primers that hybridize to the tags that have been added to the fragments, where the primer used for PCR have 5' tails that are compatible with a particular sequencing platform. Methods of performing ATAC-seq are set forth in PCT Application No. PCT/US2014/038825, which is incorporated by reference herein in its entirety.

The term "chromatin," as used herein, refers to a complex of molecules including proteins and polynucleotides (e.g. DNA, RNA), as found in a nucleus of a eukaryotic cell. Chromatin is composed in part of histone proteins that form nucleosomes, genomic DNA, and other DNA binding proteins (e.g., transcription factors) that are generally bound to the genomic DNA.

Contiguity-preserving transposition sequencing (CPT-seq) refers to a method of sequencing while preserving contiguity information by the use of transposase to maintain the association of template nucleic acid fragments adjacent in the target nucleic acid. For example, CPT may be carried out on a nucleic acid, such as on DNA or RNA. The CPT-nucleic acid can be captured by hybridization of complimentary oligonucleotides having unique indexes or barcodes and immobilized on a solid support. In some embodiments, the oligonucleotide immobilized on the solid support may further comprise primer-binding sites, unique molecular indices, in addition to barcodes. Advantageously, such use of transposomes to maintain physical proximity of fragmented nucleic acids increases the likelihood that fragmented nucleic acids from the same original molecule, e.g., chromosome, will receive the same unique barcode and index information from the oligonucleotides immobilized on a solid support. This will result in a contiguously-linked sequencing library with unique barcodes. The contiguously-linked sequencing library can be sequenced to derive contiguous sequence information.

As used herein the term "contiguity information" refers to a spatial relationship between two or more DNA fragments based on shared information. The shared aspect of the information can be with respect to adjacent, compartmental and distance spatial relationships. Information regarding these relationships in turn facilitates hierarchical assembly or mapping of sequence reads derived from the DNA fragments. This contiguity information improves the efficiency and accuracy of such assembly or mapping because traditional assembly or mapping methods used in association with conventional shotgun sequencing do not take into account the relative genomic origins or coordinates of the individual sequence reads as they relate to the spatial relationship between the two or more DNA fragments from which the individual sequence reads were derived.

Therefore, according to the embodiments described herein, methods of capturing contiguity information may be accomplished by short-range contiguity methods to determine adjacent spatial relationships, mid-range contiguity methods to determine compartmental spatial relationships, or long-range contiguity methods to determine distance spatial relationships. These methods facilitate the accuracy and quality of DNA sequence assembly or mapping, and may be used with any sequencing method, such as those described herein.

Contiguity information includes the relative genomic origins or coordinates of the individual sequence reads as they relate to the spatial relationship between the two or more DNA fragments from which the individual sequence reads were derived. In some embodiments, contiguity information includes sequence information from non-overlapping sequence reads.

In some embodiments, the contiguity information of a target nucleic acid sequence is indicative of haplotype information. In some embodiments, the contiguity information of a target nucleic acid sequence is indicative of genomic variants.

Figure 10:
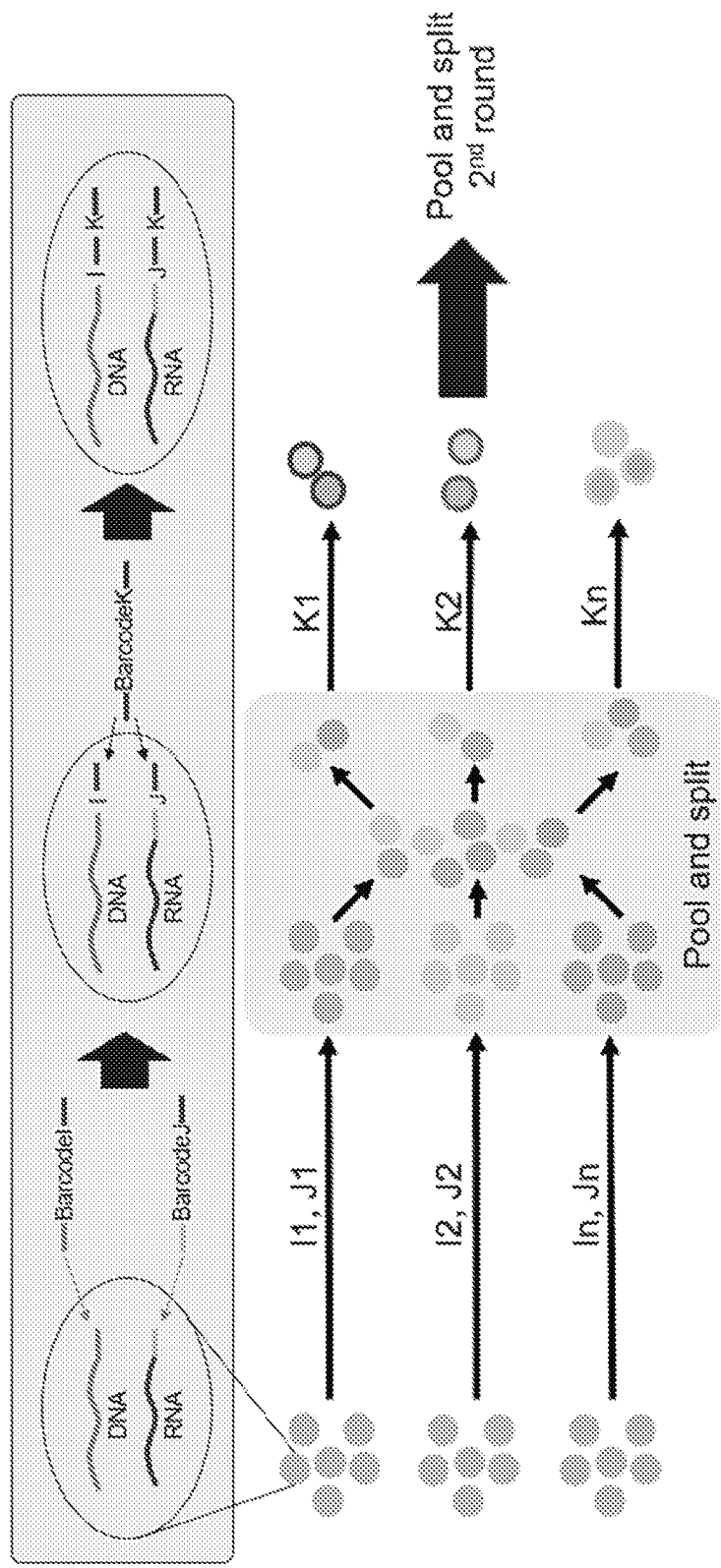
FIG. 10 is a schematic that illustrates an embodiment of a co-assay performed using combinatorial indexing, such as SCI-seq.

Single cell combinatorial indexed sequencing (SCI-seq) is a sequencing technique for simultaneously generating thousands of low-pass single cell libraries for somatic copy number variant detection. Some embodiments provided herein relate to methods, compositions, and systems for simultaneous analysis of multiple analytes in a sample using a combinatorial indexing approach, such as by SCI-seq. For example, as shown in FIG. 10, DNA and RNA can be indexed simultaneously using SCI-seq. After introduction of specific tags for DNA and RNA, the cells/nuclei are separated physically into multiple groups. For each group, DNA is labelled with a first barcode (BarcodeI in FIG. 10), and RNA is labelled with a second barcode (BarcodeJ in FIG. 10). Labelling of DNA and RNA may take place simultaneously or sequentially. The groups are then pooled together and randomly split into multiple groups, which can be further labeled with a third barcode (BarcodeK in FIG. 10). The pool and split process can be repeated for multiple rounds to increase indexing capacity. The indexing collision rate (the same barcode for different cells/nuclei) can be controlled by the number of barcodes per round and the number of cells/nuclei per group. The barcodes can be introduced by reverse transcriptase, by ligation, by tagmentation, or by other means for introducing the barcodes. In some embodiments, the combinatorial sequencing techniques described herein to not require separating or isolating nucleus from cells.

Figure 11:
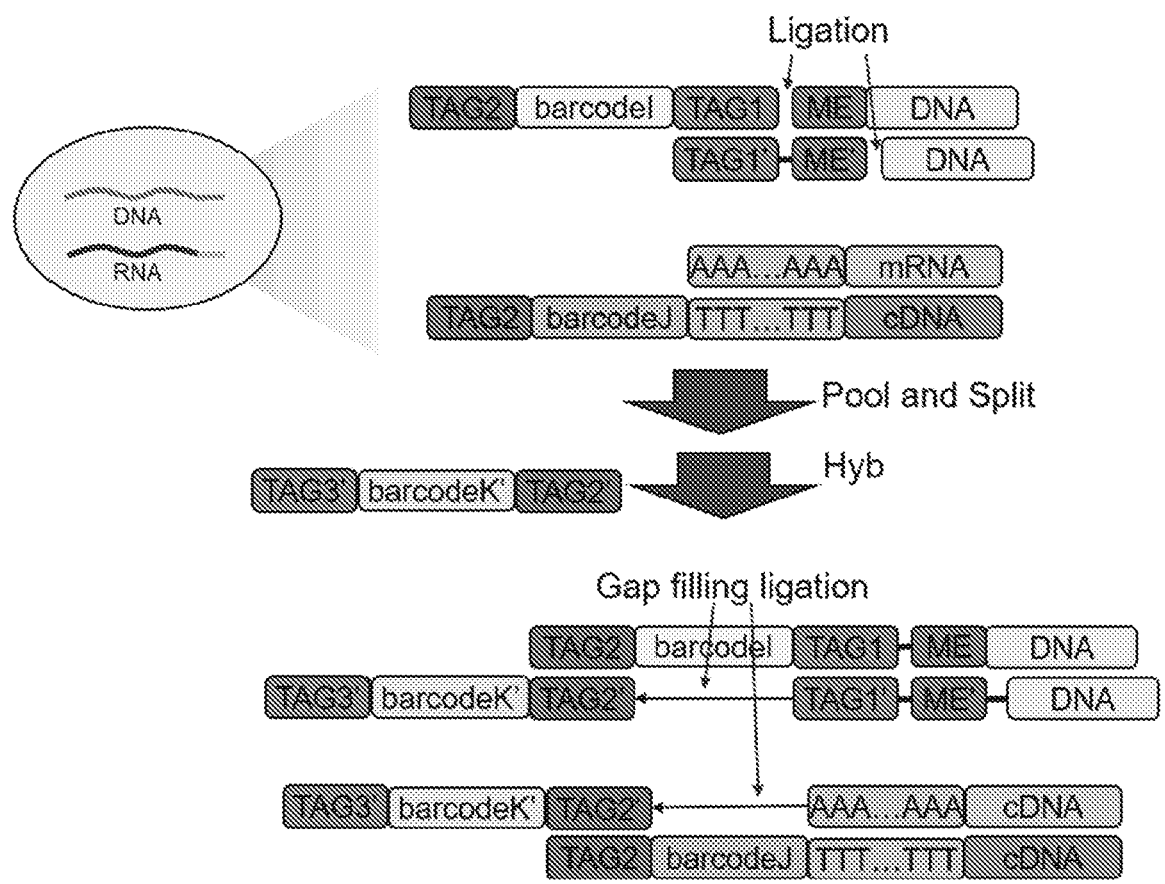
FIG. 11 is a schematic that illustrates an embodiment of a method of performing a co-assay using combinatorial sequencing.

FIG. 11 further illustrates details of combinatorial sequencing, such as by SCI-seq, with indexing by ligation and extension. A transposon with TAG1 is inserted into genomic DNA by transposition. The oligonucleotide with barcodeI and TAG2 is ligated to gDNA via TAG1 hybridization. A first cDNA synthesis is initiated by the polyT oligonucleotide with barcodeJ and TAG2, following by a second cDNA synthesis. Following a pool and split process, the oligonucleotide with barcodeK is hybridized to both gDNA and cDNA on the TAG2 region and ligated through gap filling ligation. TAG3 can serve as an anchor for next round indexing after split and pool. After combinatorial indexing, the PCR/library adapter on the other end can be added by a second transposition.

As used herein, the terms "isolated," "to isolate," "isolation," "purified," "to purify," "purification," and grammatical equivalents thereof as used herein, unless specified otherwise, refer to the reduction in the amount of at least one contaminant (such as protein and/or nucleic acid sequence) from a sample or from a source (e.g., a cell) from which the material is isolated. Thus, purification results in an "enrichment," for example, an increase in the amount of a desirable protein and/or nucleic acid sequence in the sample.

Following lysis and isolation of nucleic acids, amplification may be performed, such as multiple displacement amplification (MDA), which is a widely used technique for amplifying low quantities of DNA, especially from single cells. In some embodiments, the nucleic acids are amplified, sequenced, or used for the preparation of nucleic acid libraries. As used herein, the terms "amplify" or "amplified" "amplifying" as used in reference to a nucleic acid or nucleic acid reactions, refer to in vitro methods of making copies of a particular nucleic acid, such as a target nucleic acid, for example, by an embodiment of the present invention. Numerous methods of amplifying nucleic acids are known in the art, and amplification reactions include polymerase chain reactions, ligase chain reactions, strand displacement amplification reactions, rolling circle amplification reactions, multiple annealing and looping based amplification cycles (MALBAC), transcription-mediated amplification methods such as NASBA, loop mediated amplification methods (e.g., "LAMP" amplification using loop-forming sequences. The nucleic acid that is amplified can be DNA comprising, consisting of, or derived from DNA or RNA or a mixture of DNA and RNA, including modified DNA and/or RNA. The products resulting from amplification of a nucleic acid molecule or molecules (for example, "amplification products"), whether the starting nucleic acid is DNA, RNA or both, can be either DNA or RNA, or a mixture of both DNA and RNA nucleosides or nucleotides, or they can comprise modified DNA or RNA nucleosides or nucleotides. A "copy" does not necessarily mean perfect sequence complementarity or identity to the target sequence. For example, copies can include nucleotide analogs such as deoxyinosine or deoxyuridine, intentional sequence alterations (such as sequence alterations introduced through a primer comprising a sequence that is hybridizable, but not complementary, to the target sequence, and/or sequence errors that occur during amplification.

The captured nucleic acids can be amplified according to any suitable amplification methodology known in the art. It will be appreciated that any of the amplification methodologies described herein or generally known in the art can be utilized with universal or target-specific primers to amplify nucleic acids. Suitable methods for amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354, which is incorporated herein by reference in its entirety. The above amplification methods can be employed to amplify one or more nucleic acids of interest. For example, PCR, including multiplex PCR, SDA, TMA, NASBA and the like can be utilized to amplify nucleic acids. In some embodiments, primers directed specifically to the nucleic acid of interest are included in the amplification reaction.

Other suitable methods for amplification of nucleic acids can include oligonucleotide extension and ligation, rolling circle amplification (RCA) (Lizardi et al., Nat. Genet. 19:225-232 (1998), which is incorporated herein by reference) and oligonucleotide ligation assay (OLA) technologies (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835, all of which are incorporated by reference). It will be appreciated that these amplification methodologies can be designed to amplify nucleic acids. For example, in some embodiments, the amplification method can include ligation probe amplification or oligonucleotide ligation assay (OLA) reactions that contain primers directed specifically to the nucleic acid of interest. In some embodiments, the amplification method can include a primer extension-ligation reaction that contains primers directed specifically to the nucleic acid of interest, and which are capable of passing through the hydrogel pores. As a non-limiting example of primer extension and ligation primers that can be specifically designed to amplify a nucleic acid of interest, the amplification can include primers used for the Golden- Gate assay (Illumina, Inc., San Diego, Calif.) as exemplified by U.S. Pat. Nos. 7,582,420 and 7,611,869, each of which is incorporated herein by reference in its entirety.

In some embodiments, the nucleic acids are amplified using cluster amplification methodologies as exemplified by the disclosures of U.S. Pat. Nos. 7,985,565 and 7,115,400, the contents of each of which are incorporated herein by reference in their entirety. The incorporated materials of U.S. Pat. Nos. 7,985,565 and 7,115,400 describe methods of nucleic acid amplification, which allow amplification products to be immobilized on a solid support in order to form arrays comprised of clusters or "colonies" of immobilized nucleic acid molecules. Each cluster or colony on such an array is formed from a plurality of identical immobilized polynucleotide strands and a plurality of identical immobilized complementary polynucleotide strands. The arrays so-formed are generally referred to herein as "clustered arrays". The products of solid-phase amplification reactions such as those described in U.S. Pat. Nos. 7,985,565 and 7,115,400 are so-called "bridged" structures formed by annealing of pairs of immobilized polynucleotide strands and immobilized complementary strands, both strands being immobilized on the solid support at the 5' end, preferably via a covalent attachment. Cluster amplification methodologies are examples of methods wherein an immobilized nucleic acid template is used to produce immobilized amplicons. Other suitable methodologies can also be used to produce immobilized amplicons from immobilized DNA fragments produced according to the methods provided herein. For example, one or more clusters or colonies can be formed via solid-phase PCR whether one or both primers of each pair of amplification primers are immobilized.

Additional amplification methods include isothermal amplification. Exemplary isothermal amplification methods that can be used include, but are not limited to, multiple displacement amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587, each of which is incorporated herein by reference in its entirety. Other non-PCR-based methods that can be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyperbranched strand displacement amplification which is described in, for example Lage et al., Genome Research 13:294-307 (2003), each of which is incorporated herein by reference in its entirety. Isothermal amplification methods can be used with the strand-displacing Phi 29 polymerase or Bst DNA polymerase large fragment, 5'→3' exo— for random primer amplification of genomic DNA. The use of these polymerases takes advantage of their high processivity and strand displacing activity. High processivity allows the polymerases to produce fragments that are 10-20 kb in length. As set forth above, smaller fragments can be produced under isothermal conditions using polymerases having low processivity and strand-displacing activity such as Klenow polymerase. Additional description of amplification reactions, conditions and components are set forth in detail in the disclosure of U.S. Pat. No. 7,670,810, which is incorporated herein by reference in its entirety. In some embodiments, random hexamers are annealed to the denatured DNA followed by strand displacement synthesis at a constant temperature in the presence of a catalyzing enzyme, Phi 29. This results in DNA amplification as confirmed by an increase in the fluorescence intensity (DNA stained with SYTOX) after MDA. Independently, NEXTERA® based tagmentation after lysis and clean up and subsequent gDNA amplification via PCR as indicated by a substantial increase in fluorescence intensity after NEXTERA® tagmentation and PCR may also be performed.

Another nucleic acid amplification method that is useful in the present disclosure is Tagged PCR which uses a population of two-domain primers having a constant 5' region followed by a random 3' region as described, for example, in Grothues, et al. Nucleic Acids Res. 21(5): 1321-2 (1993), incorporated herein by reference in its entirety. The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers can be removed and further replication can take place using primers complementary to the constant 5' region.

In some embodiments, the nucleic acids are sequenced in full or in part. The nucleic acids can be sequenced according to any suitable sequencing methodology, such as direct sequencing, including sequencing by synthesis, sequencing by ligation, sequencing by hybridization, nanopore sequencing and the like.

One sequencing methodology is sequencing-by-synthesis (SBS). In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template.

One or more amplified nucleic acids can be subjected to an SBS or other detection technique that involves repeated delivery of reagents in cycles. For example, to initiate a first SBS cycle, one or more labeled nucleotides, DNA polymerase, etc., can be flowed into/through a droplet that houses one or more amplified nucleic acid molecules. Those sites where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flowcell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with amplicons produced by the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210, 891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be adapted for application of pyrosequencing to amplicons produced according to the present disclosure are described, for example, in WIPO Pat. App. Ser. No. PCT/US11/57111, US 2005/0191698 A1, U.S. Pat. Nos. 7,595,883, and 7,244,559, each of which is incorporated herein by reference.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zero mode waveguides (ZMWs). Techniques and reagents for FRET-based sequencing are described, for example, in Levene et al. Science 299, 682-686 (2003); Lundquist et al. Opt. Lett. 33, 1026-1028 (2008); Korlach et al. Proc. Natl. Acad. Sci. USA 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available. Examples of such sequencing systems are pyrosequencing (e.g. commercially available platform from 454 Life Sciences a subsidiary of Roche), sequencing using γ-phosphate-labeled nucleotides (e.g. commercially available platform from Pacific Biosciences) and sequencing using proton detection (e.g. commercially available platform from Ion Torrent subsidiary of Life Technologies) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

Another sequencing technique is nanopore sequencing (see, for example, Deamer et al. Trends Biotechnol. 18, 147-151 (2000); Deamer et al. Acc. Chem. Res. 35:817-825 (2002); Li et al. Nat. Mater. 2:611-615 (2003), the disclosures of which are incorporated herein by reference). In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore. (U.S. Pat. No. 7,001,792; Soni et al. Clin. Chem. 53, 1996-2001 (2007); Healy, Nanomed. 2, 459-481 (2007); Cockroft et al. J. Am. Chem. Soc. 130, 818-820 (2008), the disclosures of which are incorporated herein by reference).

Exemplary methods for array-based expression and genotyping analysis that can be applied to detection according to the present disclosure are described in U.S. Pat. Nos. 7,582, 420; 6,890,741; 6,913,884 or 6,355,431 or US Pat. Pub. Nos. 2005/0053980 A1; 2009/0186349 A1 or US 2005/0181440 A1, each of which is incorporated herein by reference.

In the methods of isolating nucleic acids, amplification, and sequencing as described herein, various reagents are used for nucleic acid isolation and preparation. Such reagents may include, for example, lysozyme, proteinase K, random hexamers, polymerase (for example, Φ29 DNA polymerase, Taq polymerase, Bsu polymerase), transposase (for example, Tn5), primers (for example, P5 and P7 adaptor sequences), ligase, catalyzing enzyme, deoxynucleotide triphosphates, buffers, or divalent cations.

Adaptors can include sequencing primer sites, amplification primer sites, and indexes. As used herein an "index" can include a sequence of nucleotides that can be used as a molecular identifier and/or barcode to tag a nucleic acid, and/or to identify the source of a nucleic acid. In some embodiments, an index can be used to identify a single nucleic acid, or a subpopulation of nucleic acids. In some embodiments, a single cell may be used for combinatorial indexing, for example, using a contiguity preserving transposition (CPT-seq) approach.

Indexes can be useful to identify the source of a nucleic acid molecule. In some embodiments, an adaptor can be modified to prevent the formation of concatemers, for example by the addition of blocking groups that prevent extension of the adaptor at one or both ends. Examples of 3' blocking groups include a 3'-spacer C3, a dideoxynucleotide, and attachment to a substrate. Examples of 5' blocking groups include a dephosphorylated 5' nucleotide, and attachment to a substrate.

An example method includes dephosphorylating the 5' ends of target nucleic acids to prevent the formation of concatemers in subsequent ligation steps; ligating first adaptors to the 3' ends of the dephosphorylated targets using a ligase, in which the 3' ends of the first adaptors are blocked; re-phosphorylating of the 5' ends of the ligated targets; ligating a second adaptor to the 5' ends of the dephosphorylated targets using the single-stranded ligase, in which the 5' ends of the second adaptors are non-phosphorylated.

Another example includes partial digestion of the nucleic acid with a 5' exonuclease to form a double-stranded nucleic acid with single-stranded 3' overhangs. An adaptor containing a 3' blocking group can be ligated to the 3' ends of double-stranded nucleic acid with 3' overhangs. The double-stranded nucleic acid with 3' overhangs with ligated adaptors can be dehybridized to form single-stranded nucleic acids. An adaptor containing a non-phosphorylated 5' end can be ligated to the 5' end of the single-stranded nucleic acid.

Methods to dephosphorylate nucleic acids, such as the 5' nucleotide of a nucleic acid include contacting a nucleic acid with a phosphatase. Examples of phosphatases include calf intestinal phosphatase, shrimp alkaline phosphatase, Antarctic phosphatase, and APEX alkaline phosphatase (Epicentre).

Methods to ligate nucleic acids include contacting nucleic acids with a ligase. Examples of ligases include T4 RNA ligase 1, T4 RNA ligase 2, RtcB ligase, *Methanobacterium* RNA ligase, and TS2126 RNA ligase (CIRCLIGASE).

Methods to phosphorylate nucleic acids, such as the 5' nucleotide of a nucleic acid include contacting a nucleic acid with a kinase. Examples of kinases include T4 polynucleotide kinase.

Embodiments of the systems and methods provided herein include kits, containing transposition reagents and a first probe complementary to a first tag and a second probe complementary to a second tag, wherein the first and second probes are immobilized on a solid support. In some embodiments, the first probe and the second probe comprise a barcode. In some embodiments, the first probe and second probe is a polyT probe. In some embodiments, the solid support is an etched surface, a well, an array, a flowcell device, a microfluidic channel, a bead, a magnetic bead, a column, a droplet, or a microparticle.

EXAMPLES

Example 1—Simultaneous DNA and RNA Library Preparation from Bulk Cells

The following example demonstrates an embodiment of simultaneously analyzing DNA and RNA in a sample of bulk cells.

Figure 6A:
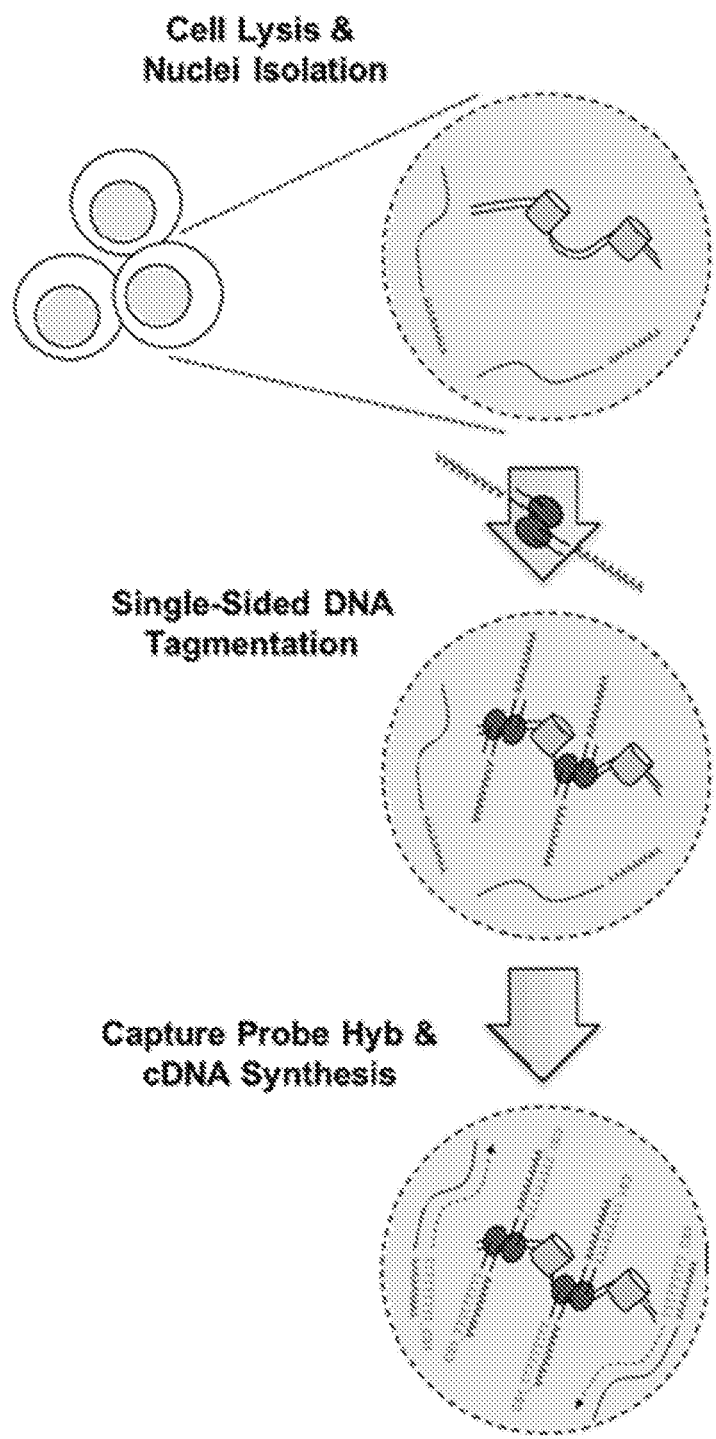
FIGS. 6A-6B show a schematic diagram depicting an embodiment of bulk co-assay.

Cells were obtained and lysed to isolate the cell nuclei, as shown in FIG. 6A. Whole genome DNA (gDNA) was tagmented using transposomes with polyA transposons. Transposomes enter the nuclei and tagment open chromatin (gDNA not bound by histones).

Following tagmentation, both the gDNA and RNA contained 3' polyA tails. Both gDNA and RNA were captured using polyT capture probes, which hybridized to the 3' polyA tails of gDNA and RNA. Capture probes contained a first common sequence (CS1) for downstream amplification and molecular indexing of the samples, cells, or for molecule demultiplexing. To convert RNA to DNA, capture probes were used as primers for cDNA synthesis by reverse transcriptase.

Figure 6B:
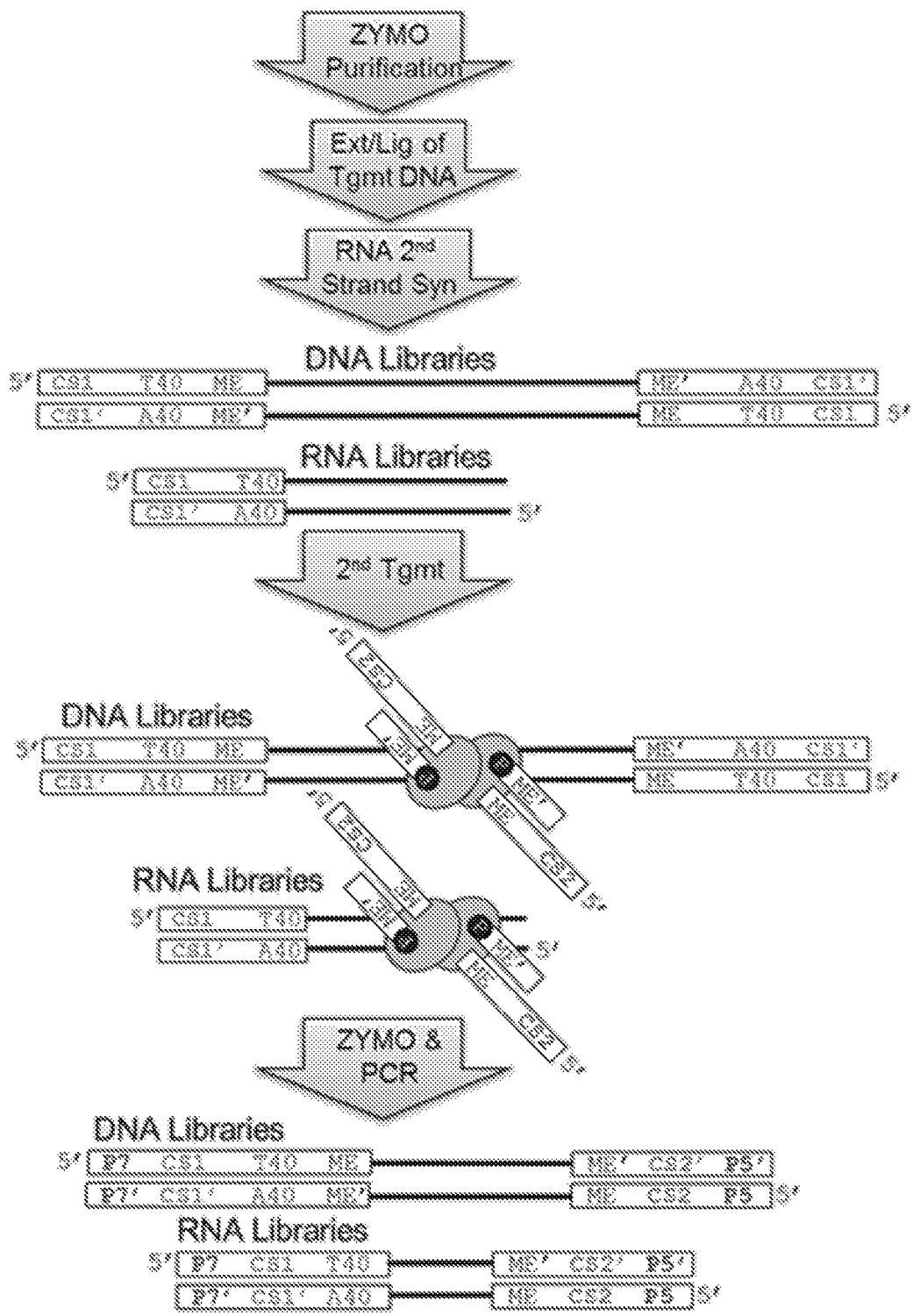

The gDNA and generated cDNA was purified from the nucleus using column purification (ZYMO), as shown in FIG. 6B. Accessible chromatic using sequencing (ATAC) library preparation was completed with an extension/ligation reaction, and RNA library preparation was completed with a second strand synthesis of cDNA. A second round of tagmentation was used to incorporate a second common sequence (CS2) and molecular indexes. Sample cleanup was performed to remove Tn5 and the final sequencing library was generated with PCR using primers complementary to CS1 and CS2.

Figure 7A:
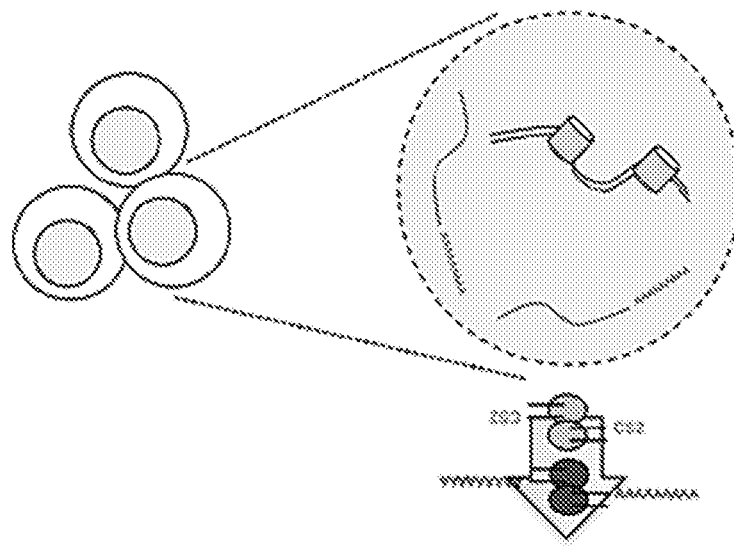
FIGS. 7A-7B show a schematic diagram depicting an embodiment of on bead coassay.
Figure 7A:
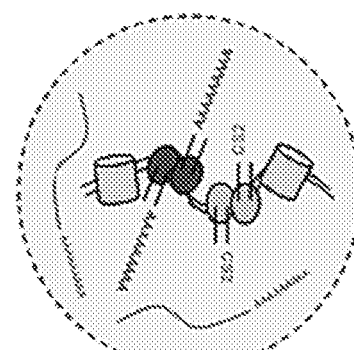
Figure 7A:
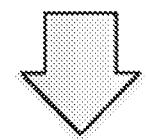
Figure 7A:
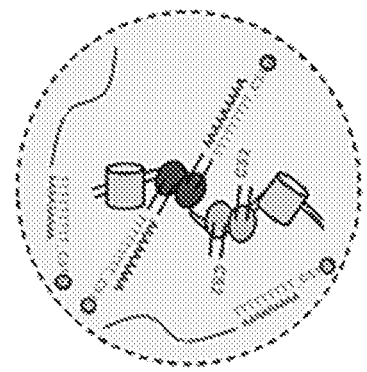
Figure 7B:
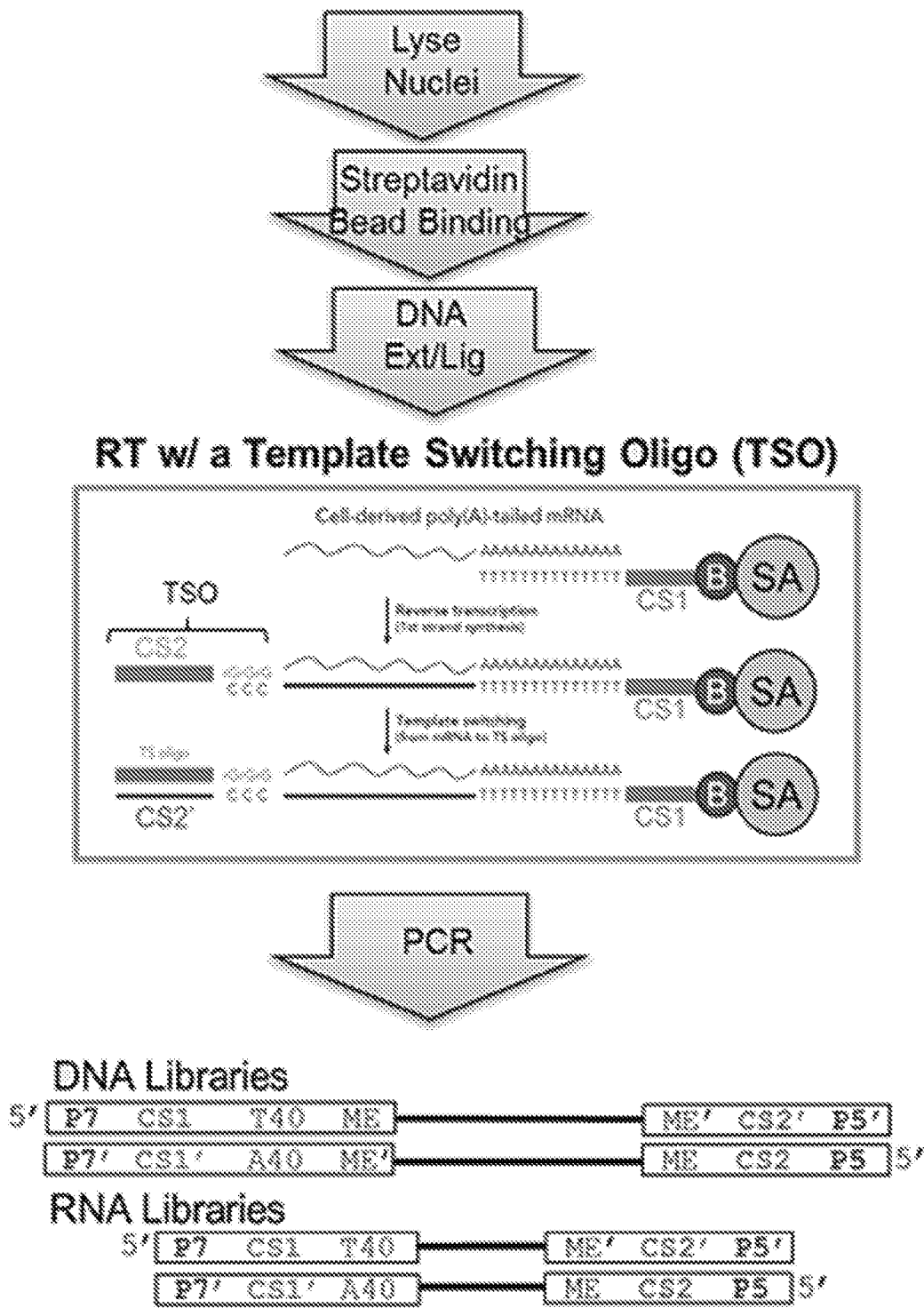

Similar methodologies were also used to simultaneously analyze DNA and RNA on bead. As shown in FIGS. 7A and 7B, the analysis can be performed for improving sample handling and/or to enable full-length RNA libraries. As shown in the schematic of FIGS. 7A and 7B, the cells were obtained and lysed to isolate nuclei. gDNA was tagmented with two transposomes containing polyA transposons and a common sequence (CS2). Transposomes enter the nuclei and tagment open chromatin (gDNA not bound by histones). Capture probes with polyT tails containing a common sequence (CS1) were hybridized to the polyA tail of both DNA and RNA libraries. To complete the RNA library preparation, the hybridization probes were used to prime cDNA synthesis. The second common sequence (CS2) was added to RNA libraries using the template switching activity of reverse transcriptase and a template switching oligonucleotide (TSO), which allows manufacture of full-length RNA. To improve sample handling, a biotinylated capture probe was used to bind RNA and DNA libraries to magnetic streptavidin beads. Washes, buffer exchanges, and handling was readily performed on bead bound molecules.

Figure 8:
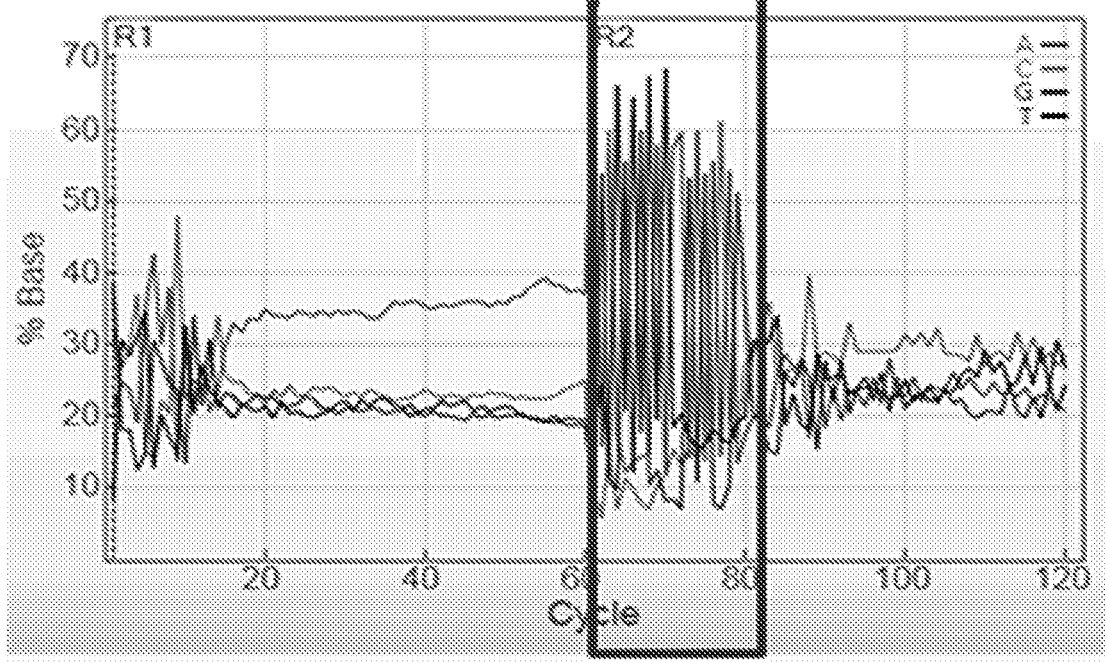
FIG. 8 depicts data from sequencing bulk co-assays of FIGS. 6A-6B. The fragment for ATAC library has a signature ME sequence, highlighted in FIG. 8.
Figure 9:
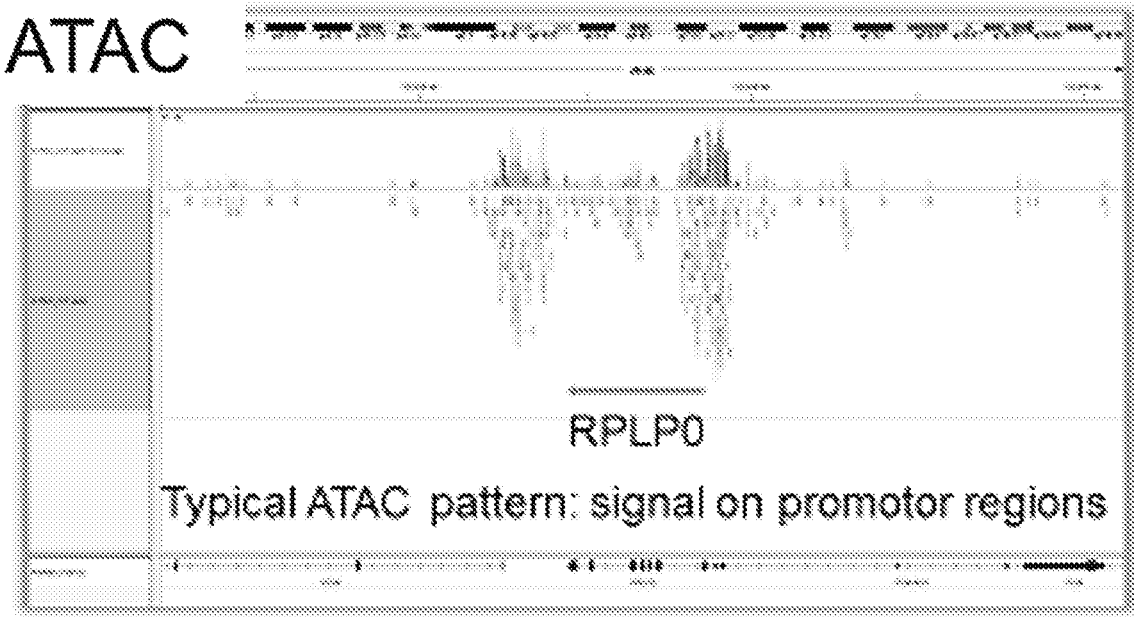
FIG. 9, panels A and B depict data from sequencing bulk co-assays of FIGS. 6A-6B. The generated library was sequenced. ATAC fragments show typical enrichment around promoter regions (panel A), and RNA fragments for 3' counting show the reads accumulation around the end of the gene (panel B).
Figure 9:
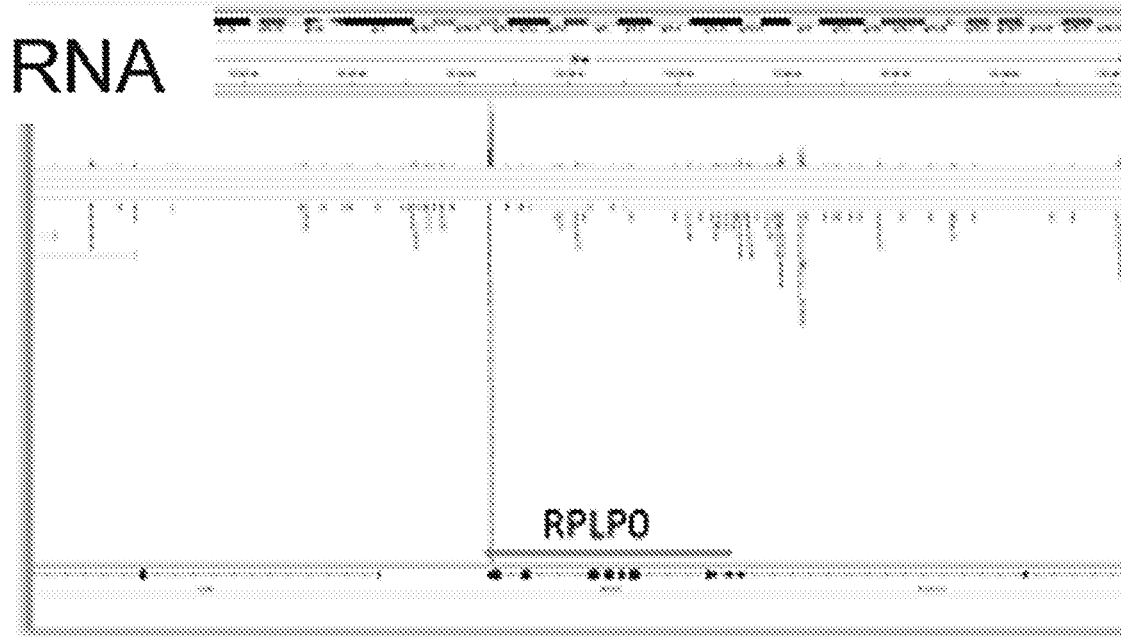

FIG. 8 depicts the results of the ATAC and RNA library preparations. The fragment for the ATAC library has a signature ME sequence, a transposon specific sequence, boxed in FIG. 8. As shown in FIG. 9, ATAC fragments show typical enrichment around promoter regions (panel A), and RNA fragments for 3' counting show the read accumulation around the end of the gene (panel B). Tables 1 and 2 summarize the results of the ATAC-seq and RNA metrics for the simultaneous DNA and RNA analysis.

TABLE 1

| ATAC-seq Metrics | |
| --- | --- |
| Total PF Reads | 4.64M |
| Read1 align %/Mismatch % | 70.02%/0.23% |
| Read2 align %/Mismatch % | 71.43%/0.47% |
| Insert Median | 159 bp |
| Dup % | 2.18% |

TABLE 2

| RNA Metrics | |
| --- | --- |
| Uniq mapped | 3.36M, ~66% |
| Multiple mapped | 0.87M, ~17% |
| Mapped to chrM | 176K, ~3.5% |
| Coding bases % | 3.4% |
| UTP bases % | 5.3% |
| Intronic bases % | 49.1% |
| Intergenic bases % | 42.2% |

Example 2—Single Cell ATAC-seq

The following example demonstrates an embodiment of performing single cell ATAC-seq in compartments.

Figure 5B:
Figure 5B:
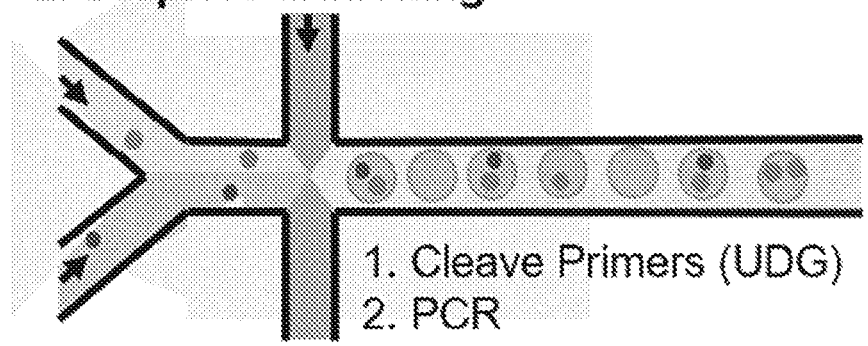
Figure 5B:
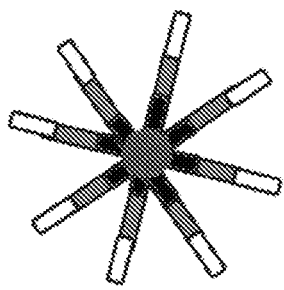

Transposition into chromatin was performed, as outlined in FIG. 5B. Following transposition, single cells or single nuclei were partitioned into compartments, in this case, into droplets. The transposase holds all individual DNA/library fragments together, thereby enabling all materials from a single cell to be encapsulated within a single droplet. All fragments from the cell in a single droplet were indexed by PCR using barcoded primers.

Figure 12:
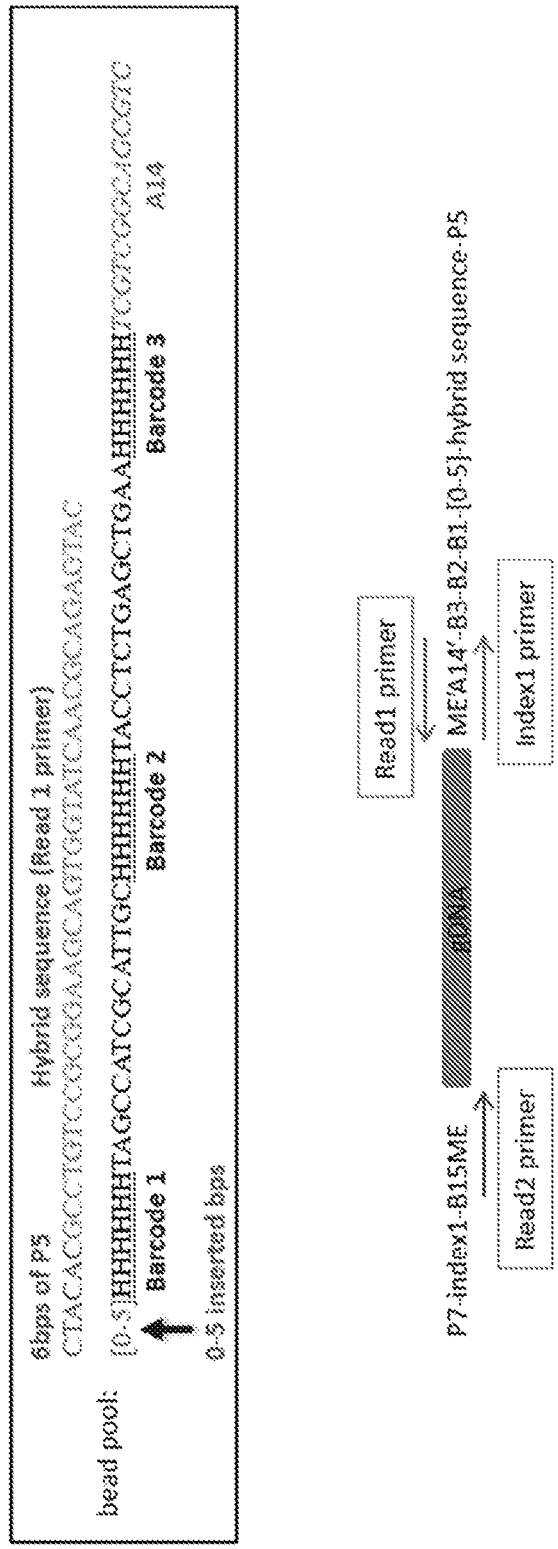
FIG. 12 depicts an exemplary embodiment of a sequencing workflow, showing a bead pool with barcodes inserted therein, and depicting exemplary primers.
Figure 13:
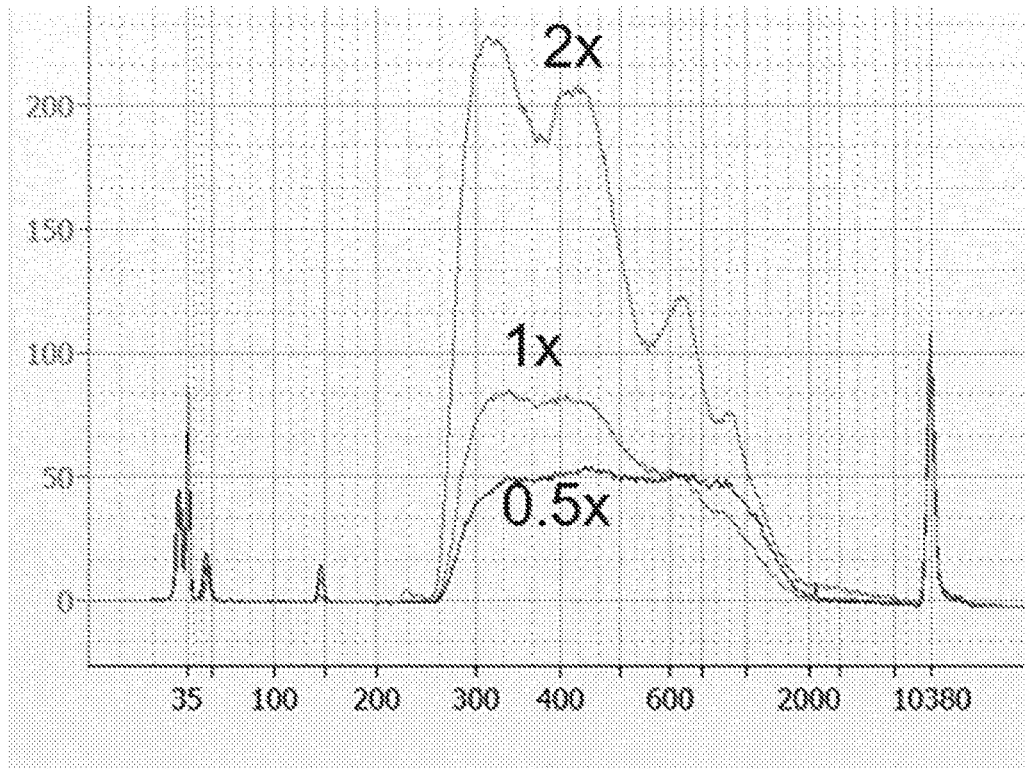
FIG. 13 shows a graph depicting number of reads per cell, showing that increasing transposase results in increased number of reads per cell.

To ensure that single cells were partitioned properly into single droplets, mixed human and mouse cells were subjected to the process. The sample included 500,000 human cells and 500,000 mouse cells. Each assay included 34,000 nuclei, which were pooled to generate one chip of droplet PCR, containing about 300,000 droplets. The assay included 140,000 beads (11 µL of 3200 beads per channel). Four cycles of droplet PCR were performed, followed by ten cycles in bulk. An example of the sequencing workflow is outlined in FIG. 12, which provides a sequence having barcodes inserted therein. It was observed that increasing Tn5 transposase increased yield, sensitivity, and percent of transcription start sites (TSS), as shown in FIG. 13.

Figure 14:
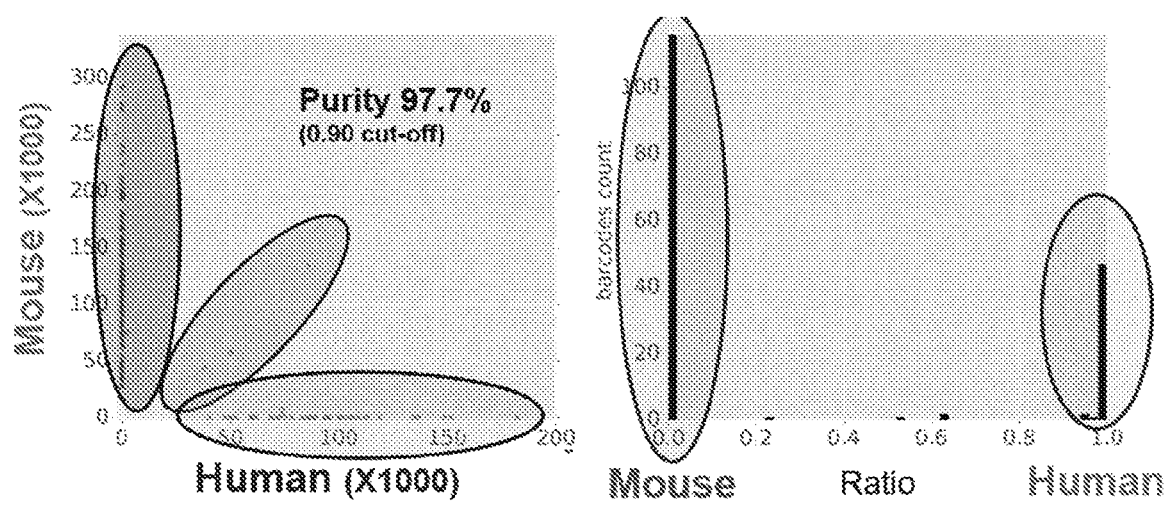
FIG. 14 shows a graph that indicates single cell sensitivity using ATAC-seq on a mixture of cell types.

Barcodes that identify the sequence reads as either from mouse or from human were read, and as outlined in FIG. 14, the results indicate that the reads aligned either to mouse or to human, indicating that a single cell was encapsulated within a single droplet, thereby enabling partitioning of single cells, which enables analysis of a single cell. As expected, ATAC read outputs were distributed around transcription start sites.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of simultaneously preparing RNA and DNA libraries in a single compartment, comprising:
   providing a sample comprising DNA and RNA, wherein the RNA comprises a 3' poly A tail;
   tagmenting the DNA with a 3' poly A tail using transposomes with poly A transposons;
   contacting the sample in a single compartment with a polyT capture probe configured to hybridize to the 3' poly A tail of the RNA and the DNA, where in the capture probe comprises a first common sequence (CS1);
   hybridizing the capture probe to the RNA and to the DNA, thereby simultaneously capturing DNA and RNA;
   converting the RNA to cDNA; and
   simultaneously generating a cDNA library and a gDNA library.

2. The method of claim 1, wherein the capture probe is immobilized on a solid support.

3. The method of claim 1, wherein the capture probe further comprises a substrate recognition sequence.

4. The method of claim 1, wherein the sample is a population of cells, a single cell, a population of cell nuclei, or a cell nucleus.

5. The method of claim 2, wherein the solid support is a substrate, an etched surface, a well, a covered well, a sealed well, an array, a flowcell device, a microfluidic channel, a bead, a magnetic bead, a column, a droplet, or a microparticle.

6. The method of claim 1, further comprising performing DNA analysis, RNA analysis, protein analysis, tagmentation, nucleic acid amplification, nucleic acid sequencing, nucleic acid library preparation, assay for transposase accessible chromatic using sequencing (ATAC-seq), contiguity-preserving transposition (CPT-seq), single cell combinatorial indexed sequencing (SCI-seq), or single cell genome amplification, or any combination thereof.

7. The method of claim 1, further comprising simultaneously analyzing in the single compartment a protein, wherein the protein is tagged.

8. The method of claim 1, wherein the sample comprises a cell, and wherein the cell is fixed with a fixative.

9. The method of claim 8, wherein the fixative comprises an alcohol, such as methanol or ethanol, or an aldehyde, such as para-formaldehyde.

10. The method of claim 1, wherein the CS1 is used for downstream amplification, molecular indexing, or molecular demultiplexing.

11. The method of claim 1, wherein the RNA is converted to cDNA by reverse transcriptase.

12. The method of claim 1, further comprising purifying the cDNA and gDNA from a cell nucleus using column purification.

13. The method of claim 1, further comprising tagmenting the cDNA and the DNA to incorporate a second common sequence (CS2) configured to generate full-length RNA, and to incorporate molecular indexes.

14. The method of claim 13, wherein the full-length RNA is generated using template switching activity of reverse transcriptase and a template switching oligonucleotide (TSO).

* * * * *

UNITED STATES PATENT AND TRADEMARK OFFICE
CERTIFICATE OF CORRECTION

| | | |
|---|---|---|
| PATENT NO. | : 12,104,281 B2 | Page 1 of 2 |
| APPLICATION NO. | : 17/250848 | |
| DATED | : October 1, 2024 | |
| INVENTOR(S) | : Frank J. Steemers et al. | |

It is certified that error appears in the above-identified patent and that said Letters Patent is hereby corrected as shown below:

On the Title Page

Column 2, Page 2, Line 57, delete "second-generaiton technologies" and insert -- second-generation technologies --.

Column 2, Page 3, Line 13, delete "an isotherma," and insert -- an isothermal, --.

Column 2, Page 3, Line 19, delete "for insertiaonl" and insert -- for insertional --.

In the Drawings

Sheet 10 of 18 (FIG. 7A), Line 8 (approx.), delete "Probe Hybridzation" and insert -- Probe Hybridization --.

In the Specification

Column 7, Line 14, delete "O-methylphosphoroamidite" and insert -- O-methylphosphoramidite --.

Column 7, Line 18, delete "xanthanine, hypoxanthanine," and insert -- xanthine, hypoxanthine, --.

Column 16, Line 7, delete "(DTS SP), ethylene" and insert -- (DTSSP), ethylene --.

Column 16, Line 56, delete "diacrylate, trimethylopropoane" and insert -- diacrylate, trimethylolpropane --.

Column 16, Line 58, delete "pentaerythritol tetracrylate," and insert -- pentaerythritol tetraacrylate, --.

Column 17, Lines 36-37, delete "diacrylate, trimethylopropoane " and insert -- diacrylate, trimethylolpropane --.

Signed and Sealed this
Seventeenth Day of December, 2024

Derrick Brent
*Acting Director of the United States Patent and Trademark Office*

Column 17, Line 38, delete "pentaerythritol tetracrylate," and insert -- pentaerythritol tetraacrylate, --.

Column 17, Line 48, delete "PEG-maleimide" and insert -- PEG-maleimide. --.

SEQUENCE LISTING

```
<160> NUMBER OF SEQ ID NOS: 8

<210> SEQ ID NO 1
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 1
tcgtcggcag cgtcagatgt gtataagaga cag                                  33

<210> SEQ ID NO 2
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 2
gtctcgtggg ctcggagatg tgtataagag acag                                 34

<210> SEQ ID NO 3
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 3
ctgtctctta tacacatct                                                  19

<210> SEQ ID NO 4
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 4
tcgtcggcag cgtc                                                       14

<210> SEQ ID NO 5
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 5
gtctcgtggg ctcgg                                                      15
```

```
<210> SEQ ID NO 6
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 6
agatgtgtat aagagacag                                               19

<210> SEQ ID NO 7
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 7
aatgatacgg cgaccaccga gauctacac                                    29

<210> SEQ ID NO 8
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 8
caagcagaag acggcatacg agat                                         24
```